(12) United States Patent
Young et al.

(10) Patent No.: US 11,058,307 B2
(45) Date of Patent: Jul. 13, 2021

(54) PRESSURE SENSING GUIDEWIRE SYSTEMS INCLUDING AN OPTICAL CONNECTOR CABLE

(71) Applicant: BOSTON SCIENTIFIC SCIMED, INC., Maple Grove, MN (US)

(72) Inventors: Misha Young, Belmont, CA (US); Peter Thornton, Jr., Los Altos, CA (US); Alfonso D'Alessandro, San Francisco, CA (US); Corey Higham, Cupertino, CA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 1179 days.

(21) Appl. No.: 15/439,486

(22) Filed: Feb. 22, 2017

(65) Prior Publication Data

US 2017/0238822 A1    Aug. 24, 2017

Related U.S. Application Data

(60) Provisional application No. 62/298,759, filed on Feb. 23, 2016.

(51) Int. Cl.
*A61B 6/00* (2006.01)
*A61B 5/0215* (2006.01)
(Continued)

(52) U.S. Cl.
CPC ........ *A61B 5/02154* (2013.01); *A61B 5/0084* (2013.01); *A61B 5/6851* (2013.01);
(Continued)

(58) Field of Classification Search
None
See application file for complete search history.

(56) References Cited

U.S. PATENT DOCUMENTS 3,963,323 A   6/1976 Arnold
4,112,941 A   9/1978 Larimore
(Continued)

FOREIGN PATENT DOCUMENTS

DE   202014100938 U1   3/2014
EP       0235992 A1   9/1987
(Continued)

OTHER PUBLICATIONS

International Search Report and Written Opinion dated May 29, 2017 from International Application No. PCT/US2017/018905.
(Continued)

*Primary Examiner* — Joel F Brutus
(74) *Attorney, Agent, or Firm* — Seager, Tufte & Wickhem, LLP

(57) ABSTRACT

Medical devices including optical connector cable assemblies are disclosed. An optical connector cable assembly may include an optical connector cable having a first optical fiber extending therefrom. The optical connector cable may include a distal connector configured to connect to a guidewire. The distal connector may include an inner housing and a guidewire locking mechanism. The distal connector may also include an actuator. Actuation of the actuator may move the inner housing from a first position to a second position. When the inner housing is in the first position the guidewire locking mechanism is configured to secure the guidewire and the guidewire is rotatable with respect to the optical connector cable. When the inner housing is in the second position the guidewire locking mechanism is in an open state for receiving or removing the guidewire.

18 Claims, 27 Drawing Sheets

(51) Int. Cl.
*A61B 5/00* (2006.01)
*A61M 25/09* (2006.01)
*A61B 90/00* (2016.01)

(52) U.S. Cl.
CPC ..... *A61M 25/09* (2013.01); *A61B 2090/3614* (2016.02); *A61B 2562/0233* (2013.01); *A61B 2562/223* (2013.01); *A61B 2562/228* (2013.01); *A61M 2025/09083* (2013.01); *A61M 2025/09116* (2013.01); *A61M 2025/09125* (2013.01)

(56) References Cited

U.S. PATENT DOCUMENTS

| | | |
|---|---|---|
| 4,771,782 A | 9/1988 | Millar |
| 4,953,553 A | 9/1990 | Tremulis |
| 5,106,455 A | 4/1992 | Jacobsen et al. |
| 5,178,159 A | 1/1993 | Christian |
| 5,238,004 A | 8/1993 | Sahatjian et al. |
| 5,313,957 A | 5/1994 | Little |
| 5,322,064 A | 6/1994 | Lundquist |
| 5,421,195 A | 6/1995 | Wlodarczyk |
| 5,422,969 A | 6/1995 | Eno |
| 5,427,114 A | 6/1995 | Colliver et al. |
| 5,438,873 A | 8/1995 | Wlodarczyk et al. |
| 5,573,520 A | 11/1996 | Schwartz et al. |
| 5,633,963 A | 5/1997 | Rickenbach et al. |
| 5,748,819 A | 5/1998 | Szentesi et al. |
| 5,755,668 A | 5/1998 | Itoigawa et al. |
| 5,772,609 A | 6/1998 | Nguyen et al. |
| 5,797,856 A | 8/1998 | Frisbie et al. |
| 5,836,885 A | 11/1998 | Schwager |
| 5,872,879 A | 2/1999 | Hamm |
| 5,873,835 A | 2/1999 | Hastings et al. |
| 5,902,248 A | 5/1999 | Millar et al. |
| 5,938,624 A | 8/1999 | Akerfeldt et al. |
| 5,949,929 A | 9/1999 | Hamm |
| 5,964,714 A | 10/1999 | Lafontaine |
| 6,112,598 A | 9/2000 | Tenerz et al. |
| 6,120,457 A | 9/2000 | Coombes et al. |
| 6,139,510 A | 10/2000 | Palermo |
| 6,162,182 A | 12/2000 | Cole |
| 6,167,763 B1 | 1/2001 | Tenerz et al. |
| 6,196,980 B1 | 3/2001 | Akerfeldt et al. |
| 6,248,083 B1 | 6/2001 | Smith et al. |
| 6,265,792 B1 | 7/2001 | Granchukoff |
| 6,312,380 B1 | 11/2001 | Hoek et al. |
| 6,394,986 B1 | 5/2002 | Millar |
| 6,398,738 B1 | 6/2002 | Millar |
| 6,409,677 B1 | 6/2002 | Tulkki |
| 6,428,336 B1 | 8/2002 | Akerfeldt |
| 6,461,301 B2 | 10/2002 | Smith |
| 6,508,803 B1 | 1/2003 | Horikawa et al. |
| 6,565,514 B2 | 5/2003 | Svanerudh et al. |
| 6,575,911 B2 | 6/2003 | Schwager |
| 6,579,246 B2 | 6/2003 | Jacobsen et al. |
| 6,579,484 B1 | 6/2003 | Tiernan et al. |
| 6,585,660 B2 | 7/2003 | Dorando et al. |
| 6,615,067 B2 | 9/2003 | Hoek et al. |
| 6,663,570 B2 | 12/2003 | Mott et al. |
| 6,766,720 B1 | 7/2004 | Jacobsen et al. |
| 6,767,327 B1 | 7/2004 | Corl et al. |
| 6,776,720 B2 | 8/2004 | Bartlett |
| 6,908,442 B2 | 6/2005 | von Malmborg et al. |
| 6,918,873 B1 | 7/2005 | Millar et al. |
| 6,918,882 B2 | 7/2005 | Skujins et al. |
| 6,974,422 B1 | 12/2005 | Millar |
| 6,976,965 B2 | 12/2005 | Corl et al. |
| 6,993,974 B2 | 2/2006 | Tenerz et al. |
| 6,994,695 B1 | 2/2006 | Millar |
| 7,071,197 B2 | 7/2006 | Leonardi et al. |
| 7,134,994 B2 | 11/2006 | Alpert et al. |
| 7,162,926 B1 | 1/2007 | Guziak et al. |
| 7,187,453 B2 | 3/2007 | Belleville |
| 7,259,862 B2 | 8/2007 | Duplain |
| 7,265,847 B2 | 9/2007 | Duplain et al. |
| 7,274,956 B2 | 9/2007 | Mott et al. |
| 7,331,236 B2 | 2/2008 | Smith et al. |
| 7,532,920 B1 | 5/2009 | Ainsworth et al. |
| 7,618,379 B2 | 11/2009 | Reynolds et al. |
| 7,684,657 B2 | 3/2010 | Donlagic et al. |
| 7,689,071 B2 | 3/2010 | Belleville et al. |
| 7,715,903 B2 | 5/2010 | Hartley et al. |
| 7,724,148 B2 | 5/2010 | Samuelsson et al. |
| 7,731,664 B1 | 6/2010 | Millar |
| 7,759,633 B2 | 7/2010 | Duplain et al. |
| 7,783,338 B2 | 8/2010 | Ainsworth et al. |
| 7,878,984 B2 | 2/2011 | Jacobsen et al. |
| 7,930,014 B2 | 4/2011 | Huenneckens et al. |
| 7,946,997 B2 | 5/2011 | Hübinette |
| 8,025,623 B1 | 9/2011 | Millar |
| 8,029,447 B2 | 10/2011 | Kanz et al. |
| 8,174,395 B2 | 5/2012 | Samuelsson et al. |
| 8,216,151 B2 | 7/2012 | Smith |
| 8,298,156 B2 | 10/2012 | Manstrom et al. |
| 8,317,715 B2 | 11/2012 | Belleville et al. |
| 8,343,076 B2 | 1/2013 | Sela et al. |
| 8,393,802 B2 | 3/2013 | Stanley et al. |
| 8,410,940 B2 | 4/2013 | Samuelsson et al. |
| 8,419,648 B2 | 4/2013 | Corl et al. |
| 8,461,997 B2 | 6/2013 | Samuelsson et al. |
| 8,485,985 B2 | 7/2013 | Manstrom et al. |
| 8,491,484 B2 | 7/2013 | Lewis |
| 8,555,712 B2 | 10/2013 | Narvaez et al. |
| 8,556,820 B2 | 10/2013 | Alpert et al. |
| 8,562,537 B2 | 10/2013 | Alpert et al. |
| 8,583,218 B2 | 11/2013 | Eberle |
| 8,585,613 B2 | 11/2013 | Nagano |
| 8,636,659 B2 | 1/2014 | Alpert et al. |
| 8,641,633 B2 | 2/2014 | Smith |
| 8,641,639 B2 | 2/2014 | Manstrom et al. |
| 8,676,299 B2 | 3/2014 | Schmitt et al. |
| 8,698,638 B2 | 4/2014 | Samuelsson et al. |
| 8,752,435 B2 | 6/2014 | Belleville et al. |
| 8,757,893 B1 | 6/2014 | Isenhour et al. |
| 8,764,683 B2 | 7/2014 | Meller et al. |
| 8,920,870 B2 | 12/2014 | Weber |
| 8,936,401 B2 | 1/2015 | Belleville et al. |
| 8,998,823 B2 | 4/2015 | Manstrom et al. |
| 9,052,466 B2 | 6/2015 | Belleville et al. |
| 9,110,255 B2 | 8/2015 | Lin et al. |
| 9,289,137 B2 | 3/2016 | Corl |
| 2003/0031422 A1 | 2/2003 | Inagaki et al. |
| 2003/0069522 A1 | 4/2003 | Jacobsen et al. |
| 2003/0077043 A1 | 4/2003 | Hamm et al. |
| 2003/0159518 A1 | 8/2003 | Sawatari et al. |
| 2004/0073141 A1 | 4/2004 | Hartley et al. |
| 2004/0167566 A1* | 8/2004 | Beulke .......... A61F 2/013 606/200 |
| 2004/0181174 A2 | 9/2004 | Davis et al. |
| 2005/0000294 A1 | 1/2005 | Tenerz et al. |
| 2005/0141817 A1 | 6/2005 | Yazaki et al. |
| 2006/0074318 A1 | 4/2006 | Ahmed et al. |
| 2006/0122537 A1 | 6/2006 | Reynolds et al. |
| 2008/0119758 A1 | 5/2008 | Samuelsson et al. |
| 2008/0285909 A1 | 11/2008 | Younge et al. |
| 2009/0082678 A1 | 3/2009 | Smith |
| 2009/0088650 A1 | 4/2009 | Corl |
| 2009/0116020 A1 | 5/2009 | Wu et al. |
| 2009/0192412 A1 | 7/2009 | Sela et al. |
| 2010/0022950 A1 | 1/2010 | Anderson et al. |
| 2010/0087605 A1 | 4/2010 | Yamamoto et al. |
| 2010/0145308 A1 | 6/2010 | Layman et al. |
| 2010/0234698 A1 | 9/2010 | Manstrom et al. |
| 2010/0241008 A1 | 9/2010 | Belleville et al. |
| 2011/0046477 A1 | 2/2011 | Hulvershorn et al. |
| 2011/0071407 A1 | 3/2011 | Hübinette et al. |
| 2011/0098572 A1 | 4/2011 | Chen et al. |
| 2011/0178413 A1 | 7/2011 | Schmitt et al. |
| 2011/0186294 A1 | 8/2011 | Narvaez et al. |
| 2011/0229094 A1 | 9/2011 | Isenhour et al. |
| 2011/0245808 A1 | 10/2011 | Voeller et al. |
| 2011/0319773 A1 | 12/2011 | Kanz et al. |
| 2012/0083794 A1 | 4/2012 | Martin et al. |

(56) References Cited

U.S. PATENT DOCUMENTS

| | | |
|---|---|---|
| 2012/0122051 A1 | 5/2012 | Hackel et al. |
| 2012/0210797 A1 | 8/2012 | Yu et al. |
| 2012/0227505 A1 | 9/2012 | Belleville et al. |
| 2012/0238869 A1 | 9/2012 | Schmitt et al. |
| 2012/0245457 A1 | 9/2012 | Crowley |
| 2012/0259273 A1 | 10/2012 | Moshinsky et al. |
| 2012/0265102 A1 | 10/2012 | Leo et al. |
| 2013/0051731 A1 | 2/2013 | Belleville et al. |
| 2013/0218032 A1 | 8/2013 | Belleville |
| 2013/0296718 A1 | 11/2013 | Ranganathan et al. |
| 2013/0296722 A1 | 11/2013 | Warnking et al. |
| 2013/0317372 A1 | 11/2013 | Eberle et al. |
| 2014/0005558 A1 | 1/2014 | Gregorich |
| 2014/0058275 A1 | 2/2014 | Gregorich et al. |
| 2014/0066789 A1 | 3/2014 | Nishigishi et al. |
| 2014/0081244 A1 | 3/2014 | Voeller et al. |
| 2014/0107624 A1 | 4/2014 | Belleville |
| 2014/0121475 A1 | 5/2014 | Alpert et al. |
| 2014/0205235 A1 | 7/2014 | Benjamin et al. |
| 2014/0241669 A1 | 8/2014 | Belleville et al. |
| 2014/0248021 A1 | 9/2014 | Belleville et al. |
| 2014/0276109 A1 | 9/2014 | Gregorich |
| 2014/0350414 A1* | 11/2014 | McGowan .......... A61B 5/02154 600/480 |
| 2015/0003783 A1 | 1/2015 | Benjamin et al. |
| 2015/0003789 A1 | 1/2015 | Webler et al. |
| 2015/0078714 A1 | 3/2015 | Isenhour et al. |
| 2015/0198774 A1 | 7/2015 | Lin et al. |
| 2015/0289929 A1* | 10/2015 | Toth .................. A61B 5/6858 600/372 |
| 2015/0301288 A1 | 10/2015 | Thornton, Jr. |
| 2015/0323747 A1 | 11/2015 | Leigh et al. |

FOREIGN PATENT DOCUMENTS

| | | |
|---|---|---|
| EP | 0738495 A1 | 10/1996 |
| EP | 0879615 A1 | 11/1998 |
| EP | 0879617 A1 | 11/1998 |
| EP | 0750879 B1 | 11/2000 |
| EP | 1136032 A1 | 9/2001 |
| EP | 1136036 A1 | 9/2001 |
| EP | 1136036 B1 | 2/2003 |
| EP | 1136032 B1 | 9/2003 |
| EP | 1479407 A1 | 11/2004 |
| EP | 1925958 A1 | 5/2008 |
| GB | 1440761 A | 6/1976 |
| GB | 2300978 A | 11/1996 |
| JP | 53141644 A | 12/1978 |
| JP | 2001507251 A | 6/2001 |
| JP | 2005533533 A | 11/2005 |
| JP | 2008514308 A | 5/2008 |
| JP | 2008304731 A | 12/2008 |
| JP | 2009010182 A | 1/2009 |
| JP | 2010233883 A | 10/2010 |
| JP | 2013132886 A | 7/2013 |
| JP | 2014525604 A | 9/2014 |
| WO | 9313707 A1 | 7/1993 |
| WO | 9533983 A1 | 12/1995 |
| WO | 9945352 A1 | 9/1999 |
| WO | 2006037082 A2 | 4/2006 |
| WO | 2007058616 A1 | 5/2007 |
| WO | 2007130163 A1 | 11/2007 |
| WO | 2008034010 A2 | 3/2008 |
| WO | 2009042865 A1 | 4/2009 |
| WO | 2011027282 A1 | 3/2011 |
| WO | 2011090744 A2 | 7/2011 |
| WO | 2011123689 A1 | 10/2011 |
| WO | 2012000798 A1 | 1/2012 |
| WO | 2012090210 A1 | 7/2012 |
| WO | 2012091783 A1 | 7/2012 |
| WO | 2013033489 A1 | 3/2013 |
| WO | 2014025255 A1 | 2/2014 |
| WO | 2015059311 A1 | 4/2015 |

OTHER PUBLICATIONS

Gregorich, Daniel J., U.S. Appl. No. 14/196,740, filed Mar. 4, 2014 entitled "Pressure Sensing Guidewire" (also published as US 2014-0276109 A1—cited above).

International Search Report and Written Opinion dated May 29, 2017 for International Application No. PCT/US2017018905.

Application filed Apr. 3, 2014 for U.S. Appl. No. 14/196,740.

* cited by examiner

PRESSURE SENSING GUIDEWIRE SYSTEMS INCLUDING AN OPTICAL CONNECTOR CABLE

CROSS-REFERENCE TO RELATED APPLICATIONS

This application claims priority under 35 U.S.C. § 119(e) to U.S. Provisional Application No. 62/298,759, filed Feb. 23, 2016, the entire disclosure of which is herein incorporated by reference.

TECHNICAL FIELD

The present disclosure pertains to medical devices, and methods for manufacturing medical devices. More particularly, the present disclosure pertains to blood pressure sensing guidewires.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An optical connector cable assembly is disclosed. The optical connector cable assembly comprises:

an optical connector cable comprising a first optical fiber extending therefrom;

wherein the optical connector cable includes a distal connector configured to connect to a guidewire, the distal connector comprising an inner housing and a guidewire locking mechanism;

an actuator, wherein actuation of the actuator moves the inner housing from a first position to a second position;

wherein when the inner housing is in the first position the guidewire locking mechanism is configured to secure the guidewire and the guidewire is rotatable with respect to the optical connector cable; and wherein when the inner housing is in the second position the guidewire locking mechanism is in an open state for receiving or removing the guidewire.

Alternatively or additionally to any of the embodiments above, the guidewire locking mechanism includes a collet closer.

Alternatively or additionally to any of the embodiments above, the guidewire locking mechanism further comprises a collet spring and a collet.

Alternatively or additionally to any of the embodiments above, the guidewire locking mechanism includes a spring loaded cam assembly.

Alternatively or additionally to any of the embodiments above, the actuator comprises a sliding mechanism, a push button, dual push buttons, a ratchet, a lever and gear assembly, or a combination thereof.

Alternatively or additionally to any of the embodiments above, further comprising an axial spring adjacent the inner housing, when the inner housing is in the second position, the axial spring collapses allowing the guidewire locking mechanism to open.

Alternatively or additionally to any of the embodiments above, the inner housing further comprises a spline gear, when the inner housing is in the second position, the spline gear prevents the inner housing from rotating relative to the optical connector cable.

Alternatively or additionally to any of the embodiments above, further comprising a collet and a collet cap, when the inner housing is in the second position, the collet cap can be rotated relative to the optical connector cable.

Alternatively or additionally to any of the embodiments above, the guidewire locking mechanism includes an offset pinch clamp.

A medical device system for measuring blood pressure is disclosed. The system comprises:

an optical connector cable including a first optical fiber and a distal connector comprising an inner housing and a guidewire locking mechanism, the distal connector capable of being coupled to a pressure sensing guidewire;

the pressure sensing guidewire including a pressure sensor and a second optical fiber extending proximally from the pressure sensor, the second optical fiber being capable of optically communicating with the first optical fiber, wherein the optical connector cable is designed to be coupled to the pressure sensing guidewire; and an actuator, wherein actuation of the actuator moves the inner housing from a first position to a second position, wherein when the inner housing is in the first position the guidewire locking mechanism is in a closed state for retaining the pressure sensing guidewire and the pressure sensing guidewire is rotatable with respect to the optical connector cable, and wherein when the inner housing is in the second position the inner housing is moved in a distal direction from the optical connector cable and the guidewire locking mechanism is in an open state for receiving or removing the pressure sensing guidewire.

Alternatively or additionally to any of the embodiments above, the guidewire locking mechanism includes a collet closer.

Alternatively or additionally to any of the embodiments above, the guidewire locking mechanism further comprises a collet spring and a collet, when the inner housing is in the second position, the collet spring is compressed allowing the collet to open, and when the inner housing is in the first position, the collet spring closes the collet closer.

Alternatively or additionally to any of the embodiments above, the guidewire locking mechanism includes a spring loaded cam assembly.

Alternatively or additionally to any of the embodiments above, the actuator comprises a sliding mechanism, a push button, dual push buttons, a ratchet, a lever and gear assembly, or a combination thereof.

Alternatively or additionally to any of the embodiments above, further comprising an axial spring adjacent the inner housing, when the inner housing is in the second position, the axial spring collapses allowing the guidewire locking mechanism to open.

Alternatively or additionally to any of the embodiments above, the inner housing further comprises a spline gear, when the inner housing is in the second position, the spline gear prevents the inner housing from rotating relative to the optical connector cable.

Alternatively or additionally to any of the embodiments above, further comprising a collet and a collet cap, when the inner housing is in the second position, the collet cap may be rotated relative to the optical connector cable.

Alternatively or additionally to any of the embodiments above, the guidewire locking mechanism includes an offset pinch clamp.

An optical connector cable is disclosed. The optical connector cable comprises:

a distal connector comprising an inner housing and a guidewire locking mechanism, the distal connector capable of being coupled to a guidewire; and an actuator, wherein actuation of the actuator moves the inner housing of the distal connector from a first position to a second position, wherein when the inner housing is in the first position the guidewire locking mechanism is in a closed state for retaining the guidewire and the guidewire is rotatable with respect to the optical connector cable, and wherein when the inner housing is in the second position the inner housing is moved in a distal direction from the optical connector cable and the guidewire locking mechanism is in an open state for receiving or removing the guidewire.

Alternatively or additionally to any of the embodiments above, the distal connector further comprises an axial spring adjacent the inner housing, when the inner housing is in the second position, the axial spring collapses allowing the guidewire locking mechanism to open.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
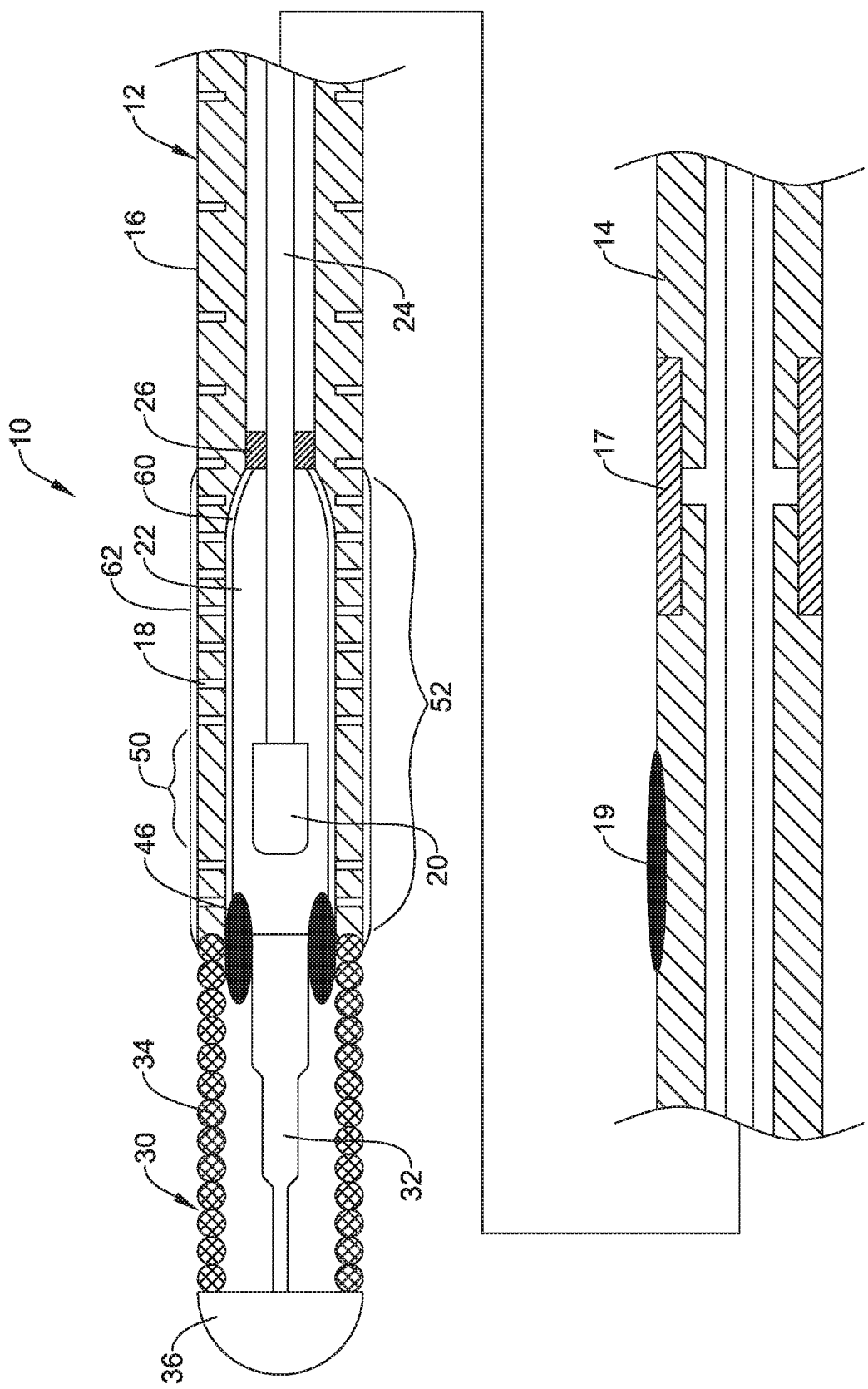
FIG. 1 is a partial cross-sectional side view of a portion of an example medical device.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the disclosure.

During some medical interventions, it may be desirable to measure and/or monitor the blood pressure within a blood vessel. For example, some medical devices may include pressure sensors that allow a clinician to monitor blood pressure. Such devices may be useful in determining fractional flow reserve (FFR), which may be understood as the ratio of the pressure after or distal of a stenosis (e.g., Pd) relative to the pressure before the stenosis and/or the aortic pressure (e.g., Pa). In other words, FFR may be understood as Pd/Pa.

FIG. 1 illustrates a portion of an example medical device 10. In this example, medical device 10 is a blood pressure sensing guidewire 10. However, this is not intended to be limiting as other medical devices are contemplated including, for example, catheters, shafts, leads, wires, or the like. Guidewire 10 may include a tubular member or shaft 12. Shaft 12 may include a proximal portion 14 and a distal portion 16. The materials for proximal portion 14 and distal portion 16 may vary and may include those materials disclosed herein. For example, proximal portion 14, distal portion 16, or both may include a nickel-cobalt-chromium-molybdenum alloy (e.g., MP35-N), a nickel-titanium alloy, stainless steel, or other materials such as those materials disclosed herein. These are just examples. Other materials may also be utilized.

In some embodiments, proximal portion 14 and distal portion 16 are formed from the same monolith of material. In other words, proximal portion 14 and distal portion 16 are portions of the same tube defining shaft 12. In other embodiments, proximal portion 14 and distal portion 16 are separate tubular members that are joined together. For example, a section of the outer surface of portions 14/16 may be removed and a sleeve 17 may be disposed over the removed sections to join portions 14/16. Alternatively, sleeve 17 may be simply disposed over portions 14/16. Other bonds may also be used including welds, thermal bonds, adhesive bonds, or the like. If utilized, sleeve 17 used to join proximal portion 14 with distal portion 16 may include a material that desirably bonds with both proximal portion 14 and distal portion 16. For example, sleeve 17 may include a nickel-chromium-molybdenum alloy (e.g., INCONEL).

A plurality of slots 18 may be formed in shaft 12. In at least some embodiments, slots 18 are formed in distal portion 16. In at least some embodiments, proximal portion 14 lacks slots 18. However, proximal portion 14 may include slots 18. Slots 18 may be desirable for a number of reasons. For example, slots 18 may provide a desirable level of flexibility to shaft 12 (e.g., along distal portion 16) while also allowing suitable transmission of torque. Slots 18 may be arranged/distributed along distal portion 16 in a suitable manner including any of those arrangements disclosed herein. For example, slots 18 may be arranged as opposing pairs of slots 18 that are distributed along the length of distal portion 16. In some embodiments, adjacent pairs of slots 18 may have a substantially constant spacing relative to one another. Alternatively, the spacing between adjacent pairs may vary. For example, more distal regions of distal portion 16 may have a decreased spacing (and/or increased slot density), which may provide increased flexibility. In other embodiments, more distal regions of distal portion 16 may have an increased spacing (and/or decreased slot density). These are just examples. Other arrangements are contemplated.

A pressure sensor 20 may be disposed within shaft 12 (e.g., within a lumen 22 of shaft 12). While pressure sensor 20 is shown schematically in FIG. 1, it can be appreciated that the structural form and/or type of pressure sensor 20 may vary. For example, pressure sensor 20 may include a semiconductor (e.g., silicon wafer) pressure senor, piezoelectric pressure sensor, a fiber optic or optical pressure sensor, a Fabry-Perot type pressure sensor, an ultrasound transducer and/or ultrasound pressure sensor, a magnetic pressure sensor, a solid-state pressure sensor, or the like, or any other suitable pressure sensor.

As indicated above, pressure sensor 20 may include an optical pressure sensor. In at least some of these embodiments, an optical fiber 24 may be attached to pressure sensor 20 and may extend proximally therefrom. An attachment member 26 may attach optical fiber 24 to shaft 12. Attachment member 26 may be circumferentially disposed about and attached to optical fiber 24 and may be secured to the inner surface of shaft 12 (e.g., distal portion 16). In at least some embodiments, attachment member 26 is proximally spaced from pressure sensor 20. Other arrangements are contemplated. In some instance, a centering ring (not shown) may be disposed around optical fiber 24 at a position that is spaced proximally from optical pressure sensor 20.

In at least some embodiments, distal portion 16 may include a region with a thinned wall and/or an increased inner diameter that defines a housing region 52. In general, housing region 52 is the region of distal portion 16 that ultimately "houses" the pressure sensor (e.g., pressure sensor 20). By virtue of having a portion of the inner wall of shaft 12 being removed at housing region 52, additional space may be created or otherwise defined that can accommodate sensor 20.

In at least some embodiments, it may be desirable for pressure sensor 20 to have reduced exposure along its side surfaces to fluid pressure (e.g., from the blood). Accordingly, it may be desirable to position pressure sensor 20 along a landing region 50 defined along housing region 52. Landing region 50 may be substantially free of slots 18 so that the side surfaces of pressure sensor 20 have a reduced likelihood of being deformed due to fluid pressures at these locations. Distal of landing are 50, housing region 52 may include slots 18 that provide fluid access to pressure sensor 20.

Moreover, slots 18 may define a fluid pathway that allows blood (and/or a body fluid) to flow from a position along the exterior or outer surface of guidewire 10 (and/or shaft 12), through slots 18, and into the lumen 22 of shaft 12, where the blood can come into contact with pressure sensor 20. Because of this, no additional side openings/holes (e.g., other than slots 18) may be necessary in shaft 12 for pressure measurement. This may also allow the length of distal portion 16 to be shorter than typical sensor mounts or hypotubes that would need to have a length sufficient for a suitable opening/hole (e.g., a suitable "large" opening/hole) to be formed therein that provides fluid access to sensor 20.

A tip member 30 may be coupled to distal portion 16. Tip member 30 may include a shaping member 32 and a spring or coil member 34. A distal tip 36 may be attached to shaping member 32 and/or spring 34. In at least some embodiments, distal tip 36 may take the form of a solder ball tip. Tip member 30 may be joined to distal portion 16 of shaft 12 with a bonding member 46 such as a weld.

Shaft 12 may include a hydrophilic coating 19. In some embodiments, hydrophilic coating 19 may extend along substantially the full length of shaft 12. In other embodiments, one or more discrete sections of shaft 12 may include hydrophilic coating 19.

Figure 2:
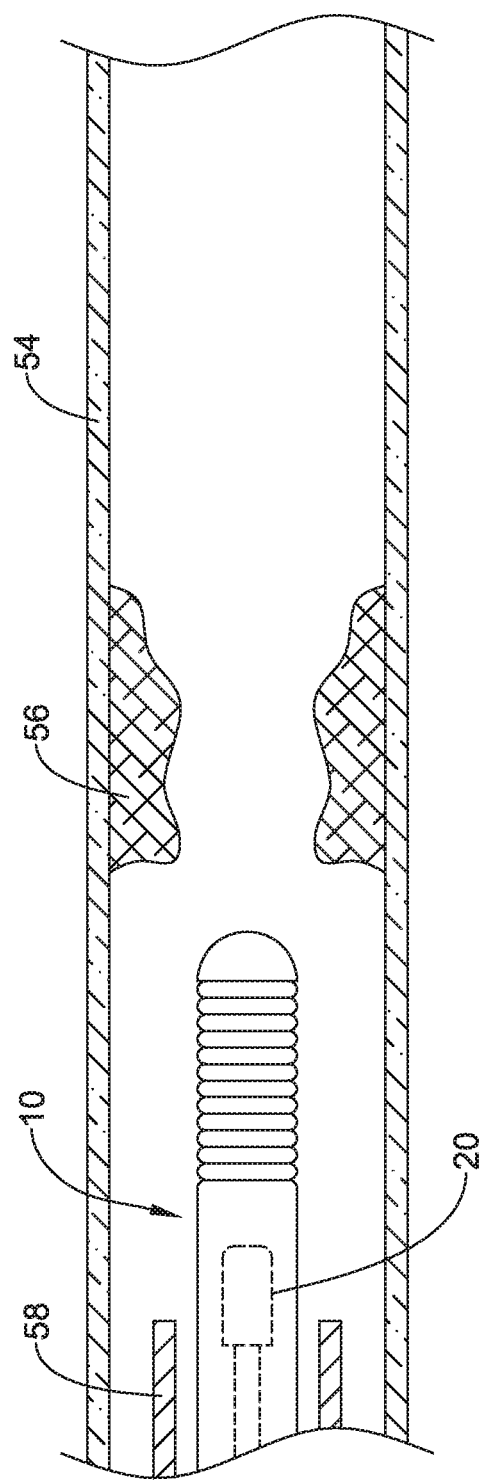
FIG. 2 is a partial cross-sectional view of an example medical device disposed at a first position adjacent to an intravascular occlusion.
Figure 3:
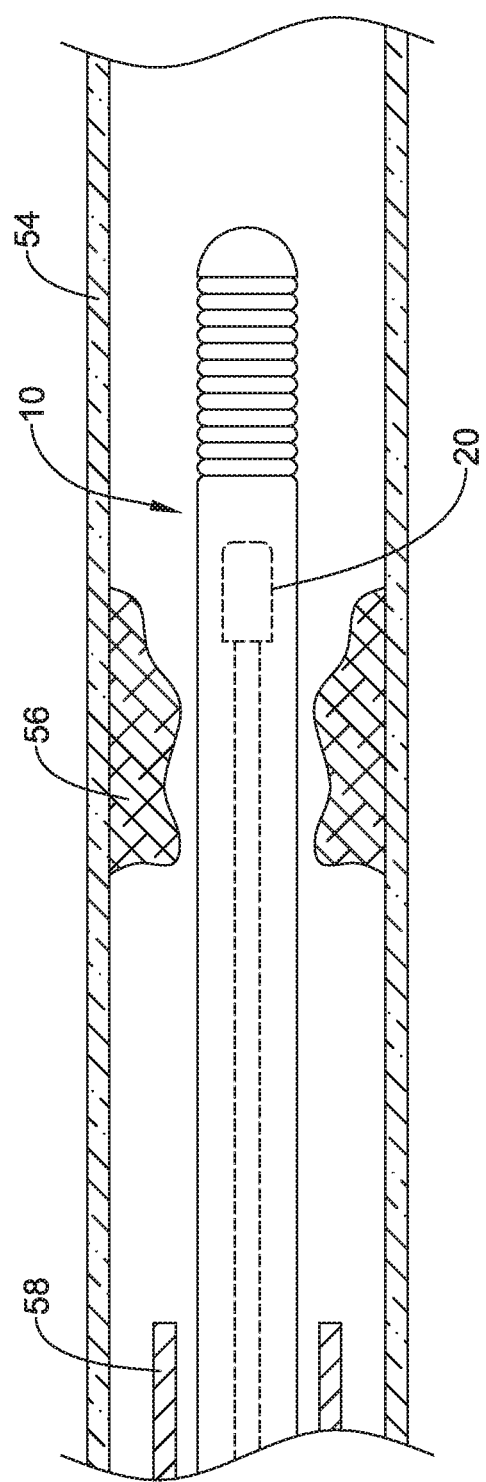
FIG. 3 is a partial cross-sectional view of an example medical device disposed at a second position adjacent to an intravascular occlusion.

In use, a clinician may use guidewire 10 to measure and/or calculate FFR (e.g., the pressure after an intravascular occlusion relative to the pressure before the occlusion and/or the aortic pressure). Measuring and/or calculating FFR may include measuring the aortic pressure in a patient. This may include advancing guidewire 10 through a blood vessel or body lumen 54 to a position that is proximal or upstream of an occlusion 56 as shown in FIG. 2. For example, guidewire 10 may be advanced through a guide catheter 58 to a position where at least a portion of sensor 20 is disposed distal of the distal end of guide catheter 58 and measuring the pressure within body lumen 54. This pressure may be characterized as an initial pressure. In some embodiments, the aortic pressure may also be measured by another device (e.g., a pressure sensing guidewire, catheter, or the like). The initial pressure may be equalized with the aortic pressure. For example, the initial pressure measured by guidewire 10 may be set to be the same as the measured aortic pressure. Guidewire 10 may be further advanced to a position distal or downstream of occlusion 56 as shown in FIG. 3 and the pressure within body lumen 54 may be measured. This pressure may be characterized as the downstream or distal pressure. The distal pressure and the aortic pressure may be used to calculate FFR.

It can be appreciated that an FFR system that utilizes an optical pressure sensor in a pressure sensing guidewire may be connected to a number of processing/conditioning units, displays, and the like. When making these connections, the various cables/connections may be designed so that the optical signals can be transmitted between adjacent optical fibers in an efficient manner.

A wide variety of optical connectors exist that are designed to allow for efficient communication between adjacent optical fibers. Such connectors are typically utilized in industries such as telecommunication. The use of optical fibers in medical devices may provide a variety of challenges. For example, when optical fibers are utilized in medical devices, it may be desirable for the connectors to allow for the connection of various devices and/or components while allowing for movement (e.g., rotation) of the components relative to one another during use. At least some of the medical devices, medical device systems, and connectors disclosed herein may include features that improve the connection of components of a fiber optic system such as the connection of a guidewire with an optical fiber to an optical connector cable.

For the purposes of this disclosure, reference will be made to "medical device systems". The medical device systems may be understood to be one or more medical devices that may be used together. In at least some embodiments, the medical device systems disclosed herein may be systems for measuring FFR. These systems may include a pressure sensing guidewire, an optical connector cable coupled to the guidewire, a signal conditioning unit and/or processing unit coupled to the optical connector cable, and a display unit or output. The systems may also include additional intermediate cables and/or devices, guide catheters, other pressure measuring devices and/or components, and the like. References made to a system are not meant to imply that all of these components are present.

Figure 4:
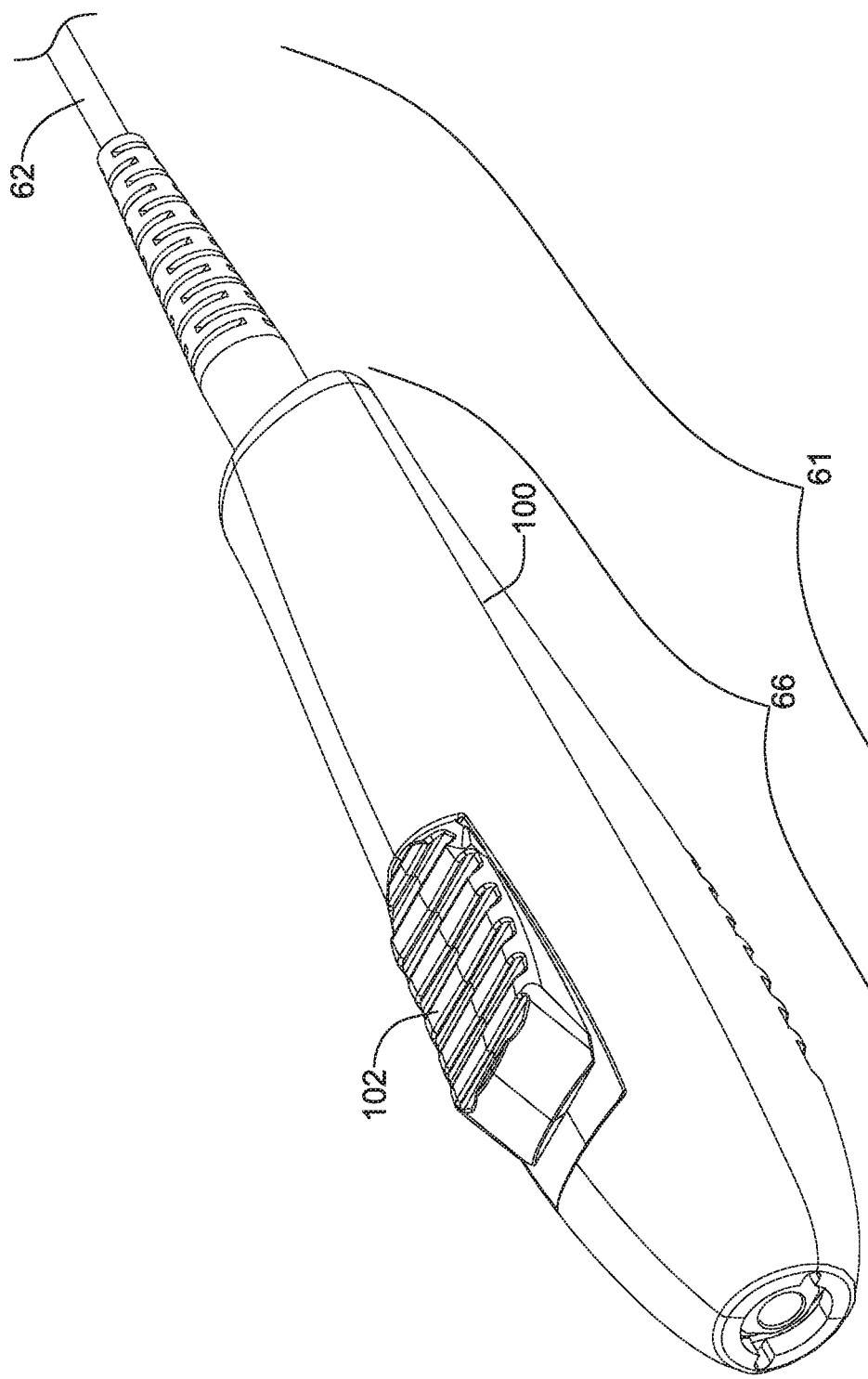
FIG. 4 is a perspective view of an example medical device system 11.

FIG. 4 is a perspective view of an example optical connector cable 61. Optical connector cable 61 is designed to be coupled to a guidewire (e.g., guidewire 10) in a manner that permits rotation of the guidewire relative to optical connector cable 61. Optical connector cable 61 includes a distal connector 66 for securing the guidewire to optical connector cable 61. Distal connector 66 may include a housing 100 and an actuator 102. Actuator 102, which may take the form of a slidable button, may be used to actuate a guidewire locking mechanism as described in more detail herein. Some example guidewire locking mechanisms contemplated are disclosed herein. A cable body 62 may extend from distal connector 66. At the proximal end of cable body 62, optical connector cable 61 may include a proximal connector (not shown) for connecting optical connector cable 61 to other components such as signal conditioning and/or processing devices.

Figure 5:
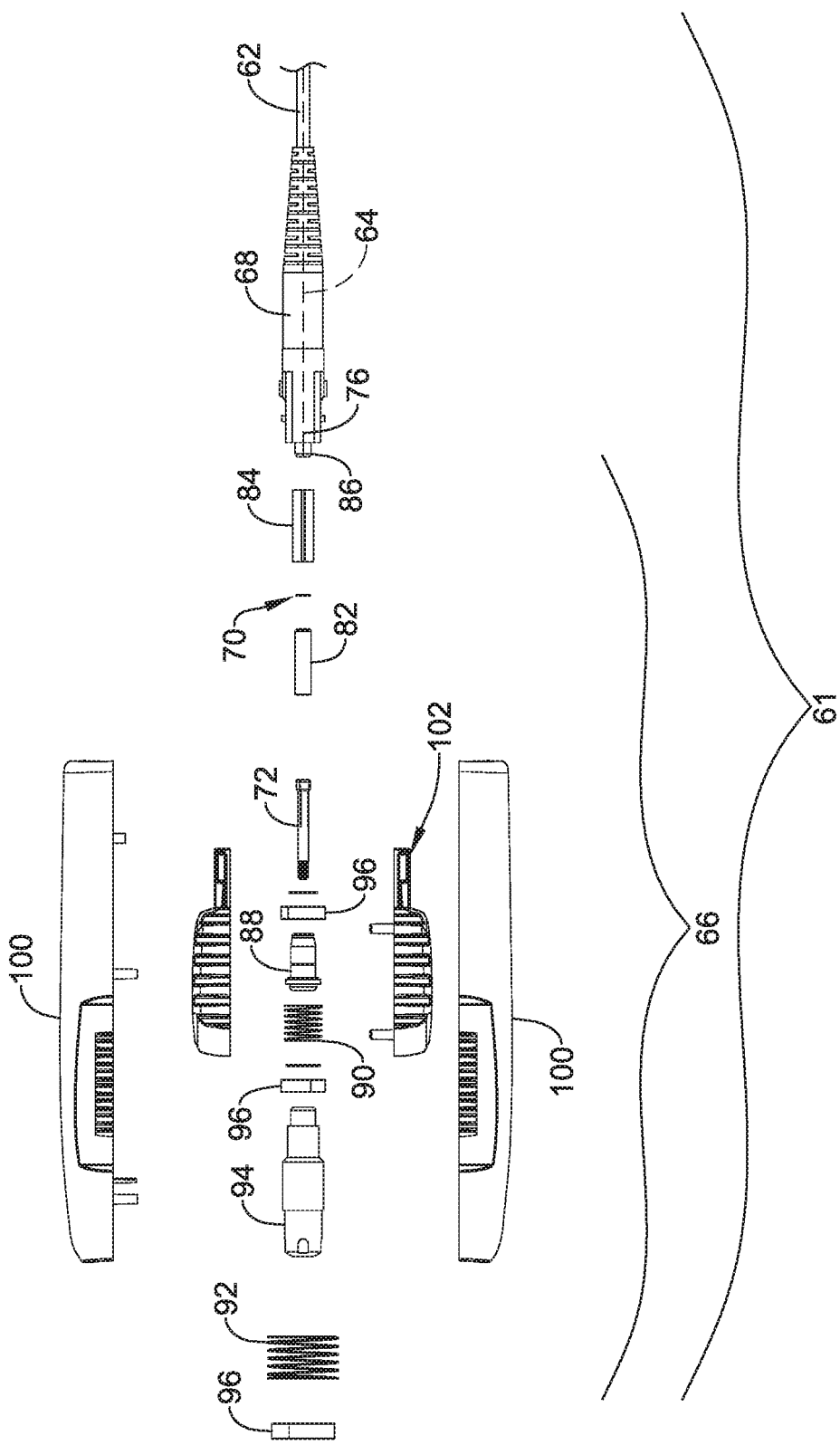
FIG. 5 is an exploded view of an example of a medical device system 11.

FIG. 5 is an exploded view of optical connector cable 61. Optical connector cable 61 may include structural features that allow connector cable 61 to communicate with other components and may optionally include a flanged body that is secured (e.g., via an adhesive bond or other suitable bond) to a ferrule 86. Connector cable 61 may be utilized to optically connect an optical fiber (e.g., optical fiber 24 within guidewire 10) with an optical fiber 64, which extends to one or more components of a medical device system (and/or other systems) including, for example, a signal conditioning unit.

Movement and/or contact between adjacent optical fibers such as fibers 24/64 could lead to damage of the polished ends of the fibers 24/64. This could impact the communication between fibers 24/64. In order to improve the communication between fibers 24/64, a coupler 70 may be disposed within distal connector 66. Coupler 70 may be disposed between the ends of fibers 24/64. In at least some embodiments, coupler 70 may be a deformable disc or cylinder. For example, coupler 70 may take the form of a polymer disc. This may include a disc or cylinder formed from a compliant material such as an optically clear (e.g., aliphatic) polyurethane. Other forms are also contemplated for coupler 70. For example, coupler 70 may be a gel (e.g., a relatively thick gel), a coating on one or both of fibers 26/64, a membrane, or the like. Coupler 70 may be formed from one or more polymers or from other suitable materials including those disclosed herein. In at least some embodiments, coupler 70 may function as a "cushioning member" or a structural feature that provides some level of deformability at the interface between fibers 24/64 when bringing together fibers 24/64 (and/or bringing together guidewire 10 and optical connector cable 61).

In can be appreciated that optical fibers 24/64 may include an inner core and an outer cladding. In some instances, optical fibers 24/64 may have cores with the same diameter (e.g., about 62.5 µm). In other instances, optical fibers 24/64 may have cores with differing diameters. For example, optical fiber 24 may have a core diameter of about 62.5 µm and optical fiber 64 may have a core diameter of about 105 µm. These are just examples. Other diameters are contemplated. In addition, the outer diameter of optical fibers 24/64 may be the same or different. For example, the outer diameter of optical fibers 24/64 may be about 125 µm. These are just examples. Other diameters are contemplated.

As indicated above, distal connector 66 may include a guidewire locking mechanism that is designed to be secured to a guidewire 10 while permitting relative rotation of guidewire 10 relative to optical connector cable 61. For example, distal connector 66 may include a guidewire locking structure for releasably locking guidewire 10 to distal connector 66. In the example embodiment shown in FIG. 5, the guidewire locking structure includes a locking collet 72. Other guidewire locking structures are contemplated including those disclosed herein. A collet retainer 94, an axial spring 92 and a pair of bearings 96 may also be disposed within housing 100.

In some instances, the locking collet 72 may be actuated with an actuator 102. In the embodiment shown in FIG. 5, for example, a sliding mechanism which can be actuated by pushing actuator 102, forward. Housed within the optical connector cable 61 is included a collet closer 88, bearings 96 and a collet spring 90. Distal connector 66 further includes a housing 100, a wire ferrule 82, a polymer disc 70, a ferrule 86, a split sleeve 84, a flanged body 76, a body 68 and a cable body 62. In some instances, an O-ring (not shown) may be disposed between the housing 100 and the body 68. The O-ring may provide additional cushioning (e.g., cushioning for a guidewire inserted into the distal connector 66 when the guidewire is urged against the coupler 70).

The optical connector cable 61, distal connector 66 and a guidewire locking mechanism 72 is couplable to a guidewire 10. In use, an actuator 102 can be employed to actuate the inner housing 74 from a first position to a second position wherein the guidewire locking mechanism 72 is open when the inner housing 74 is in the second position allowing insertion of the guidewire 10 therein, and the guidewire locking mechanism 72 is closed when the inner housing 74 and moves to the first position, which closes the guidewire locking mechanism 72 for retaining the guidewire 10. When the inner housing 74 is in the first position, the guidewire is secured to the distal connector 66 and the guidewire is rotatable relative to the distal connector 66.

Figure 6:
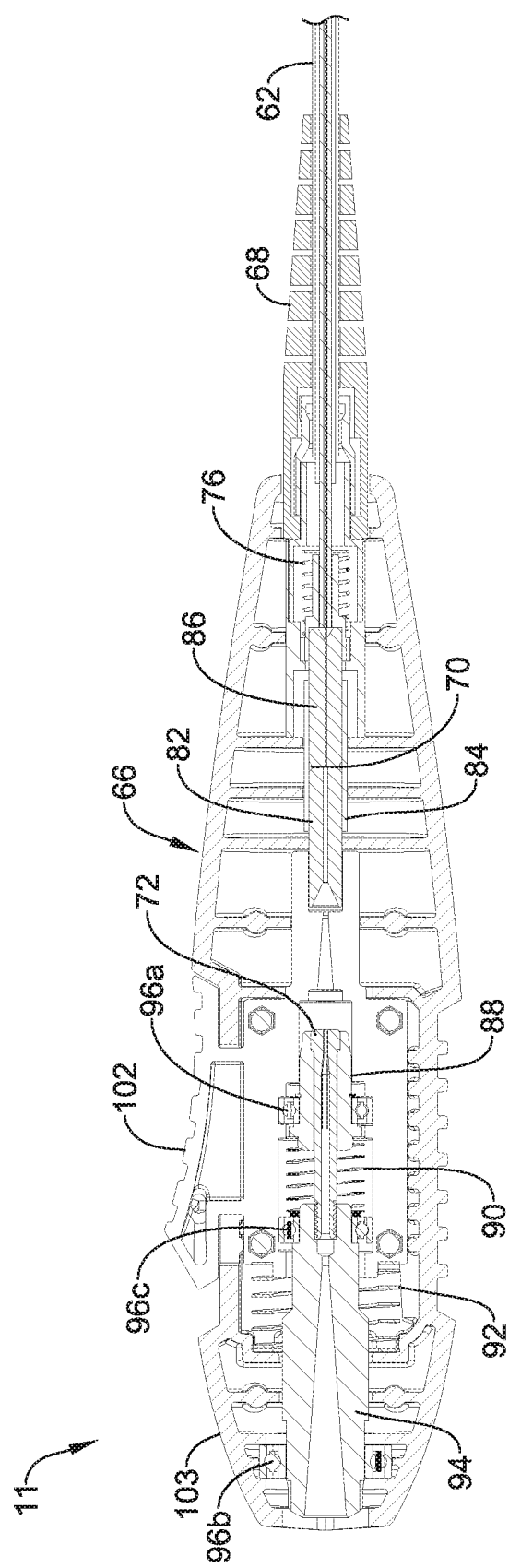
FIGS. 6-10 are cross-sectional views of an example medical device system.

FIGS. 6-10 are partial cross-sectional views of medical device 11 and the actuation of the guidewire locking mechanism. For example, FIG. 6 is a partial cross sectional view of medical device 11 before a guidewire has been inserted into distal connector 66. In this figure, the actuator 102 has not been actuated and is disposed at a first or proximal position along distal connector 66, the axial spring 92 adjacent to the distal connector housing 103 pushes (and/or otherwise exerts a force upon) the actuator 102 proximally or to the right adjacent the housing 100 and the collet 72 is closed by the collet spring 90 between the collet retainer 94 and the collet closer 88. The collet spring 90 pushes against the collet retainer 94 holding the collet retainer 94 over a portion of the collet 72 thus closing the collet 72 to lock guidewire 10 in place. Bearings such as bearings 96a/96b/96c help to keep the various structures of distal connector 66 oriented in a desired manner. When arranged as shown in FIG. 6, the distal end of the collet retainer 94 may extend to a position that is substantially flush with or proximal of the distal end of the distal connector housing 103. In some instance, the collet retainer 94 may be slightly shortened (e.g., shortened relative to what is shown in FIGS. 6-10) so that the distal end of the collect retainer 94 may extend to a position that is substantially axially aligned with a distal end or edge of the bearing 96b.

Figure 7:
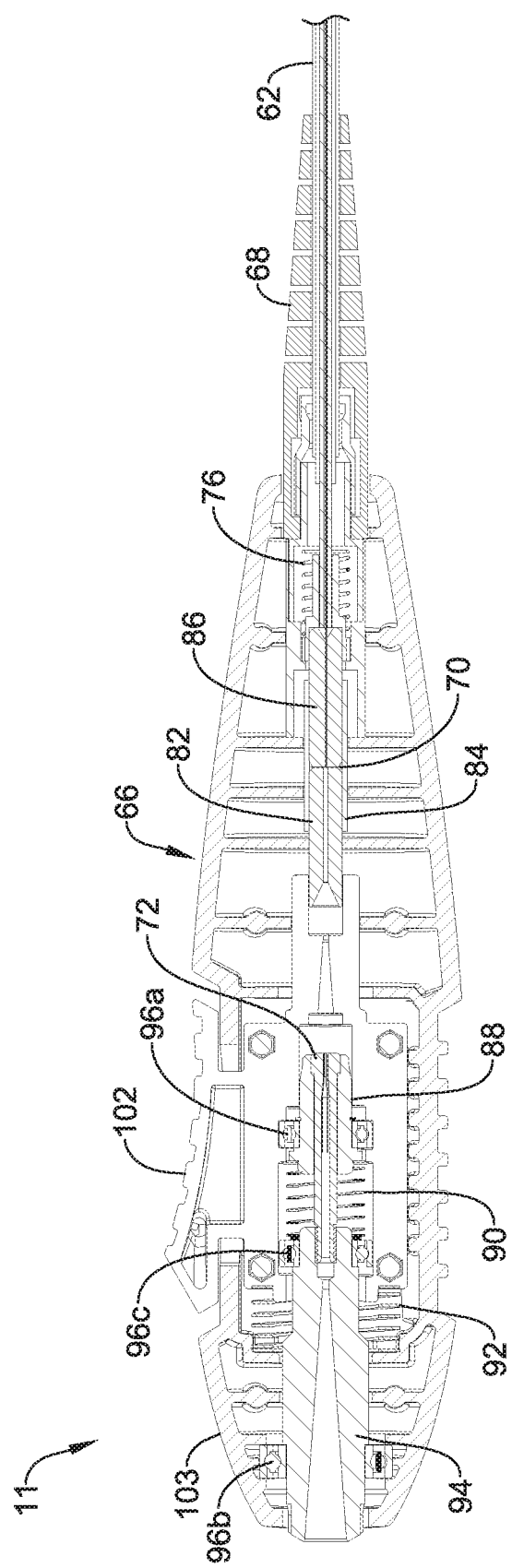
Figure 8:
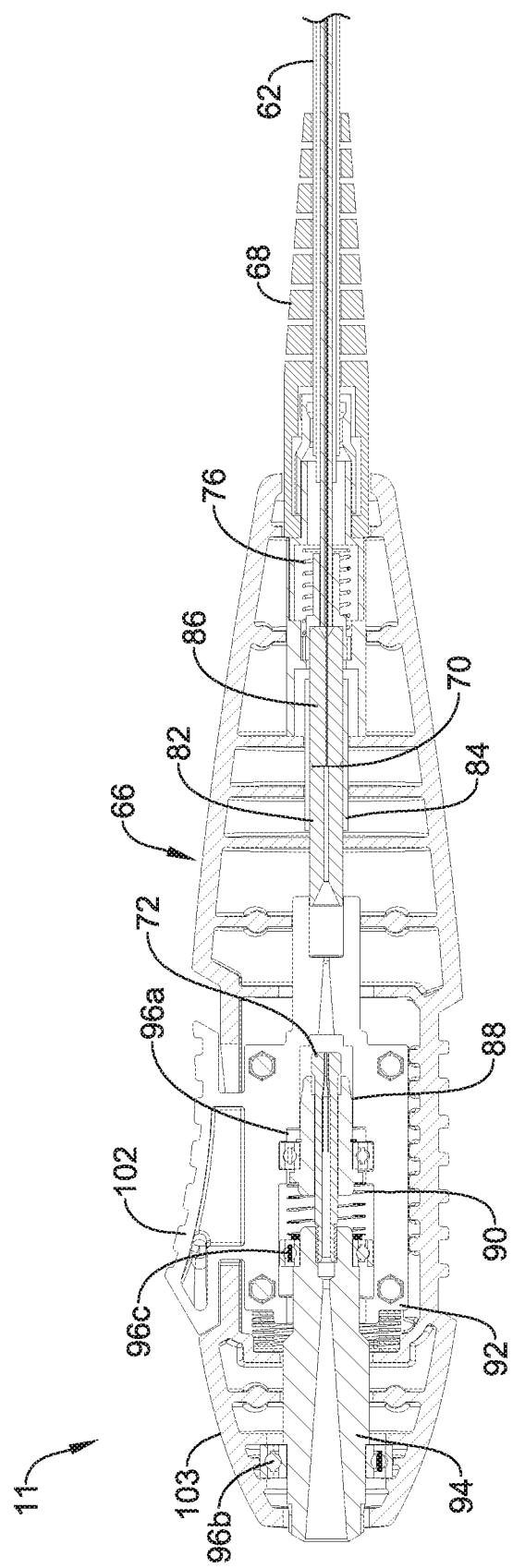

FIG. 7 is a partial cross-sectional view illustrating the actuator 102 being advanced to the point where the collet retainer 94 comes into contact with the distal bearing 96b of the actuator 102, which stops the forward motion of the collet retainer 94 and the collet 72. In some instances, the distal end of the collet retainer 94 may extend distally beyond the distal end of the distal connector housing 103 as shown in FIG. 7. Alternatively, the distal end of the collet retainer 94 may extend to a position that is substantially flush with the distal end of the distal connector housing 103 or to a position that is proximal of the distal end of the distal connector housing 103. In some of these instances, the collet retainer 94 may be slightly shortened (e.g., relative to what is shown in FIGS. 6-10) in order to be arranged in such a manner. As actuator 102 is further advanced, as shown in FIG. 8, the collet closer 88 moves distally, compressing the collet spring 90. The distal movement of the collet closer 88 allows the collet 72 to open for insertion of a guidewire 10. Once the guidewire 10 is in place, actuator 102, collet retainer 94 and collet closer 88 move proximally to close the collet 72. The guidewire 10 is gripped by the collet 72 and is stopped adjacent the polymer disc 70. The axial spring 92 pushes on the assembly so that the proximal end of the guidewire 10 is pushed into the ferrule 82 to provide the axial force necessary for achieving a good optical connection.

Figure 9:
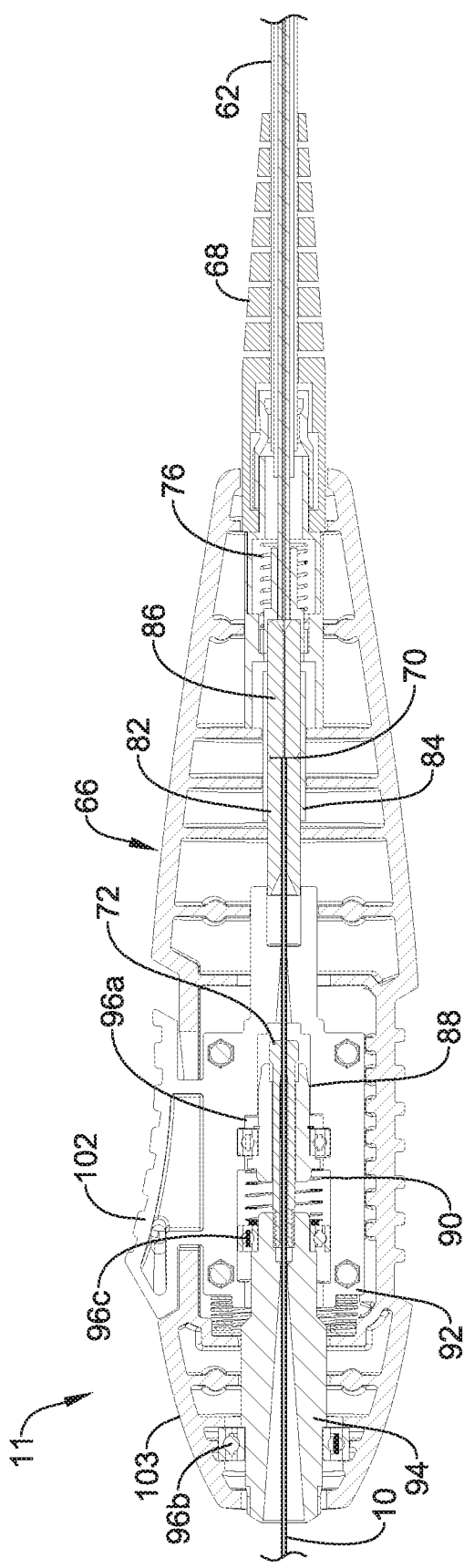
Figure 10:
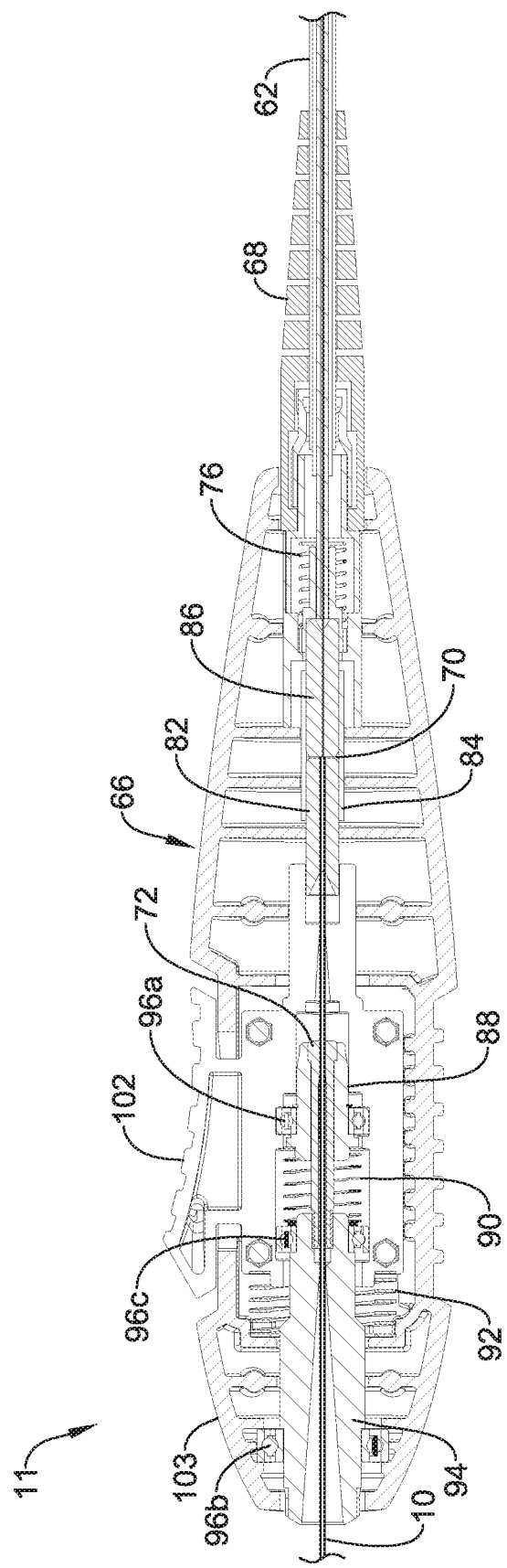

With collet 72 open, guidewire 10 may be inserted into distal connector 66 as shown in FIG. 9. Guidewire 10 is pushed in all the way into distal connector 66 until it is stopped at a position adjacent the polymer disc 70 which is disposed between the wire ferrule 82 and the ferrule 86, allowing for close contact between optical fibers (not shown) to facilitate optical communication. FIG. 10 is a partial cross-sectional view wherein the actuator 102 has been released, the collet 72 is closed to grip the guidewire 10. Releasing the actuator 102 allows the locking mechanism 88 to close and grip the guidewire 10 securing the guidewire 10 to the cable body 62. The actuator 102 and collet closer 88 move proximally which closes the collet 72 with the force generated by the collet spring 90. Once the guidewire 10 is gripped by the collet 72, the internal assembly can no longer move proximally and the axial spring 92 generates a force on the guidewire 10/optical connector cable 61 junction to ensure a good optical connection. When so positioned/connected with distal connector 66, guidewire 10 can be rotated relative to optical connector cable 61. For example, the collet retainer 94, collet spring 90, collet 72, and collet closer 88 are all free to rotate allowing guidewire 10 to rotate similarly to facilitate navigation through the vasculature without having to disconnect the guidewire 10 from optical connector cable 61.

Figure 11:
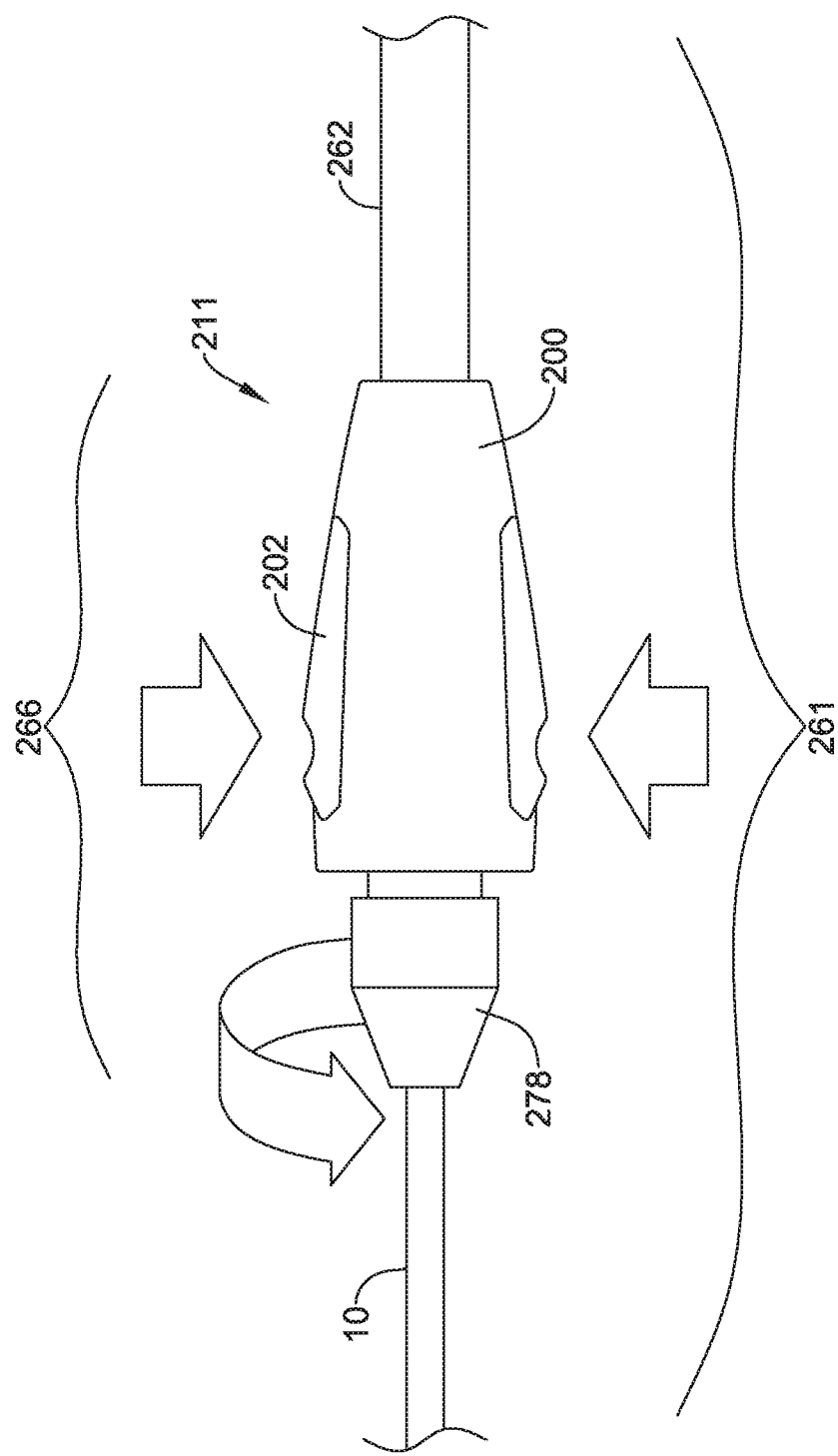
FIG. 11 is a partial cross-sectional side view of an example medical device system.

FIG. 11 is a partial side view of another example medical device system 211 having an actuator in the form of one or more buttons 202 on either side of housing 200 of the distal connector 266 which is connected to cable body 262. In some instances, a single button 202 is used. In other instances, two or more buttons 202 may be utilized. Buttons 202 may be simultaneously pressed for actuation of the guidewire locking mechanism (not shown). When the one or more buttons 202 are not pressed, the inner housing 274 is disengaged from the teeth/grooves of the spline gear 298 so that the guidewire 10 can be rotated. Pressing the buttons 202 engages the inner housing 274 with the teeth/grooves of the spline gear 298 so that the collet cap 278 can be rotated to actuate collet 272 and lock the guidewire 10. Once a guidewire 10, is inserted in the distal end of distal connector 266, the buttons 202 can be released allowing rotation of collet cap 278. The dual buttons 202 prevent accidental actuation of the inner assembly including the guidewire locking mechanisms (now shown). The example medical device is explained in more detail below with respect to FIGS. 12-14.

Figure 12:
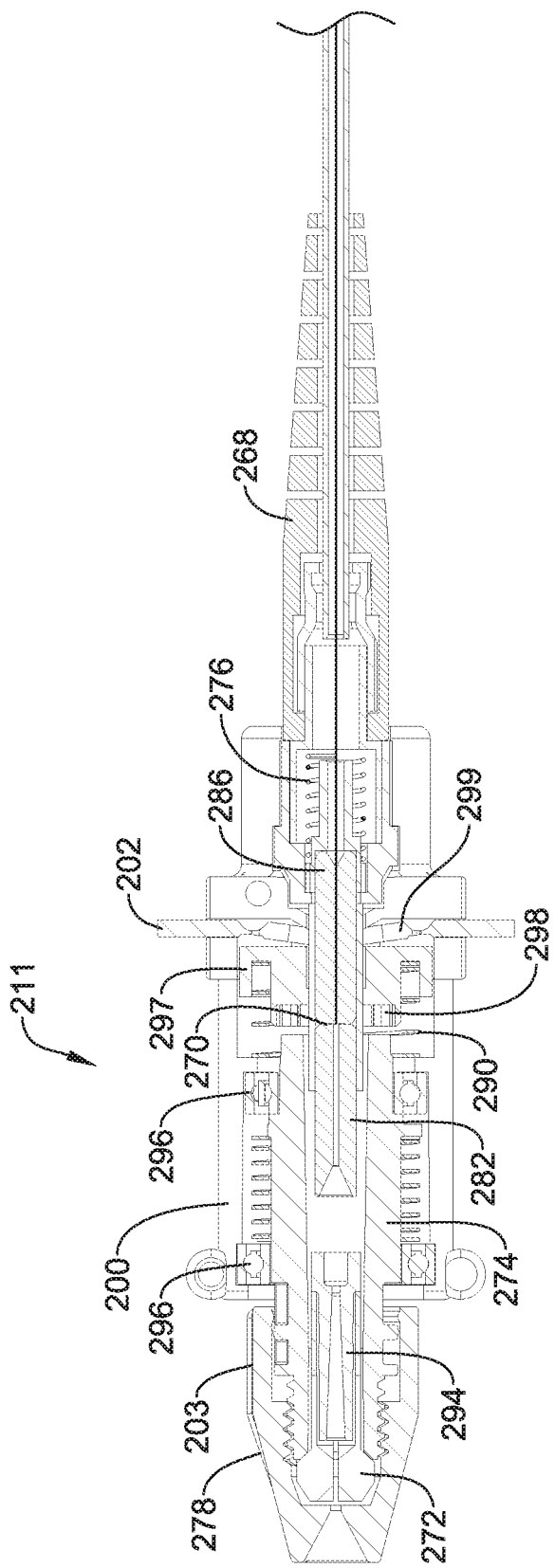
FIGS. 12-14B are partial cross-sectional side views of an example medical device system.

FIG. 12 is a partial cross-sectional view of an example medical device system 211. Medical device system 211 includes a distal connector 266 and an optical connector cable 261. Distal connector 266 includes a guidewire locking mechanism that may include a collet 272, a collet retainer 294, and a rotatable collet cap 278. Housing 200 of optical connector cable 261 includes a distal axial spring 292, a guidewire ferrule 282, an optical cable ferrule 286, a split sleeve 284, a polymer disc disposed between ferrule 282 and ferrule 286, collet spring 290, bearing assembly 296, actuator 202 in the form of dual buttons and three living hinges 299. Other configurations and/or button shapes are contemplated.

Figure 13:
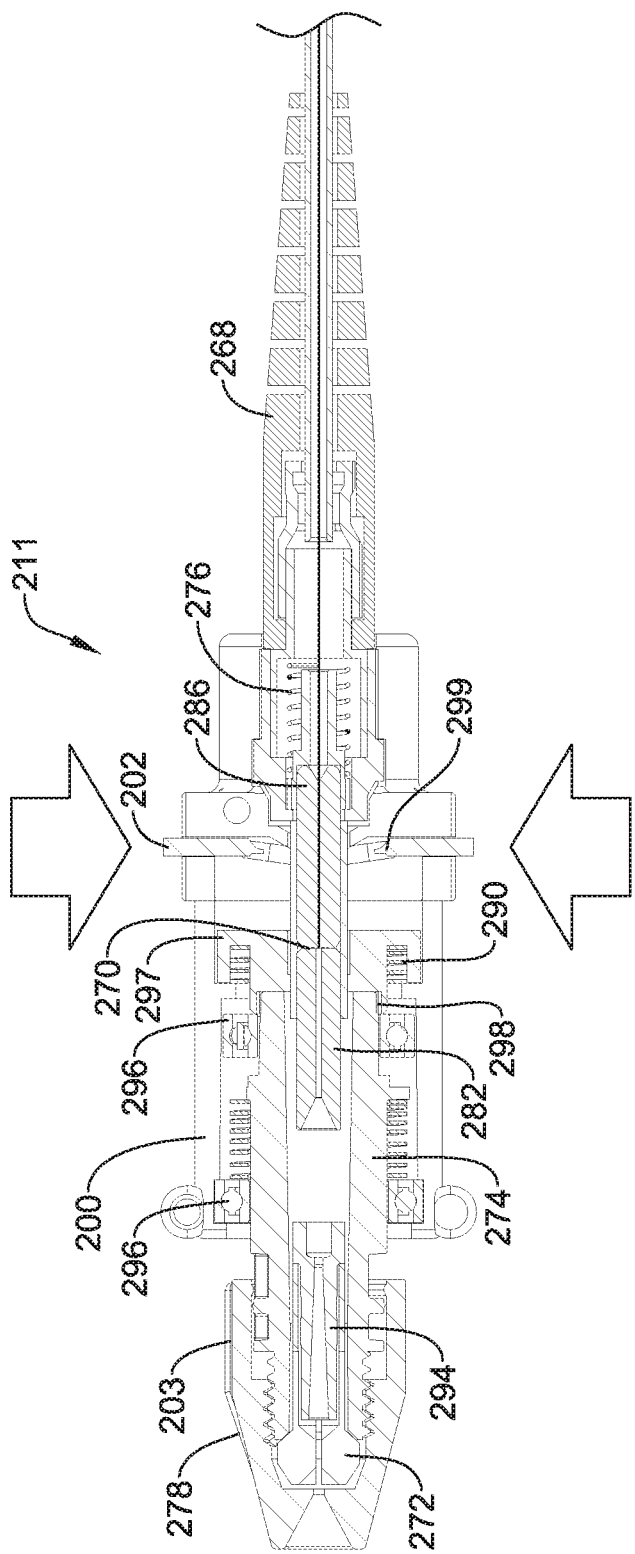
Figure 14:
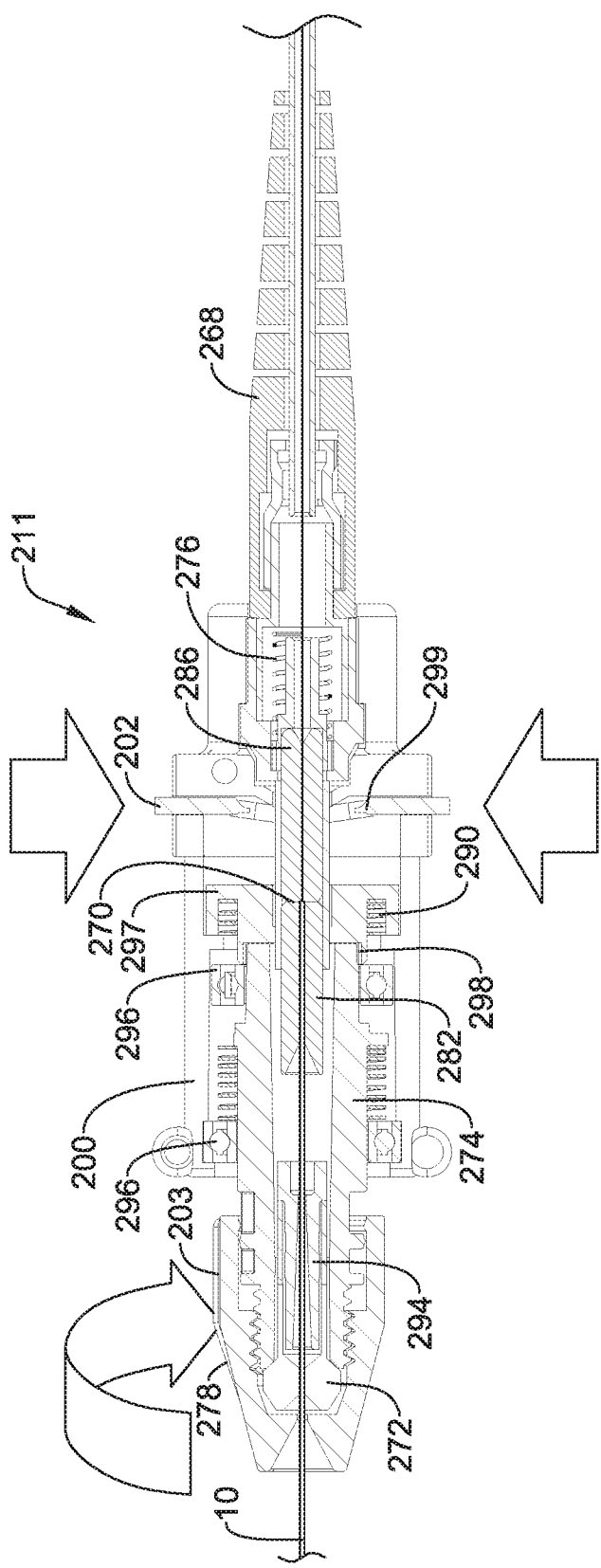
Figure 14B:
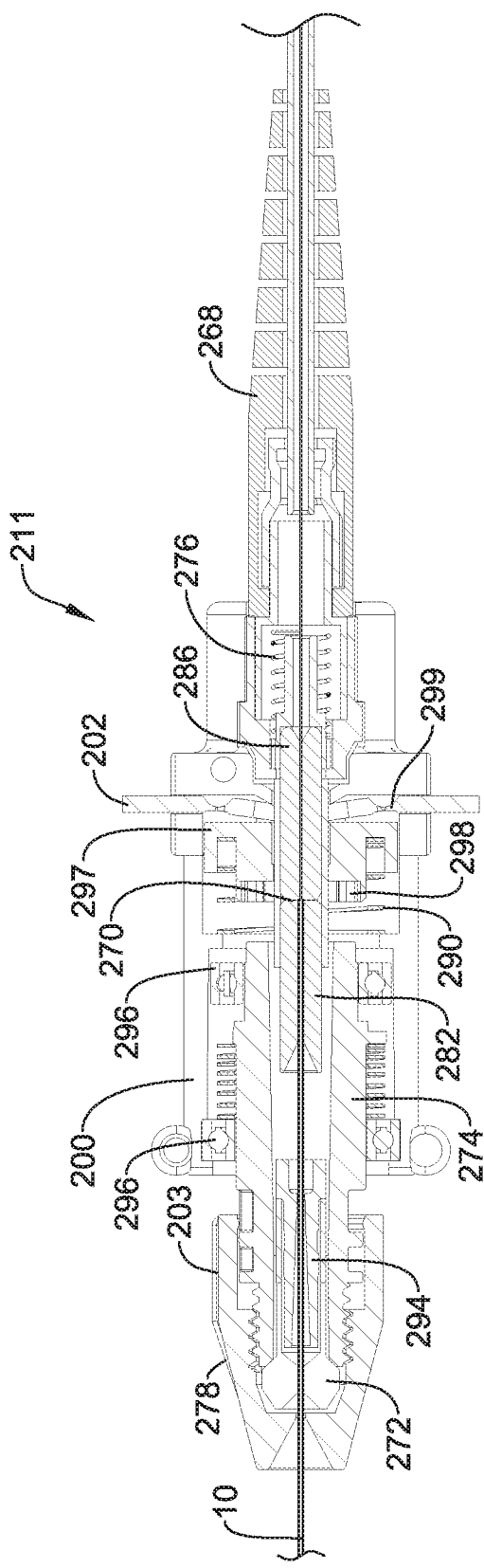

Housing 200 of distal connector further includes an inner housing 297 having a spline gear 298. Spline gear 298 prevents inner housing 274 of optical connector cable 261 from rotating when the actuator buttons 202 are fully depressed as shown in FIG. 12. When the actuator buttons 202 are depressed as shown in FIG. 13, the inner housing 297 is moved distally moving the collet 272, the inner housing 274, the collet cap 278, the collet retainer 294, and the bearing assembly 295 distally. The spline gear 298 in the inner housing 297 engages grooves in inner housing 274 which prevents rotation of the system 211 such that the collet cap 278 can be tightened by rotation to grip the guidewire 10 as shown in FIG. 14. Once the guidewire 10 is in place and the collet cap 278 tightened, the buttons 202 can be released, disengaging the spline gear 298 from the grooves in the inner housing 274, allowing the assembly to rotate. With the buttons 202 released, the guidewire 10 is gripped in the collet 272 and optical fiber 24 is in contact with the polymer disc 270 and the ferrule 282. The distal spring 292 provides axial force on the guidewire 10 against the polymer disc 270 and the ferrule 282 to ensure a good connection. FIG. 14B is a partial cross-sectional view of a medical device system 211 wherein actuator buttons 202 have been fully released and the inner housing 274 along with guidewire 10 are free to rotate for maneuverability of the guidewire 10 through a patient's body lumen without disconnecting guidewire 10.

Figure 15:
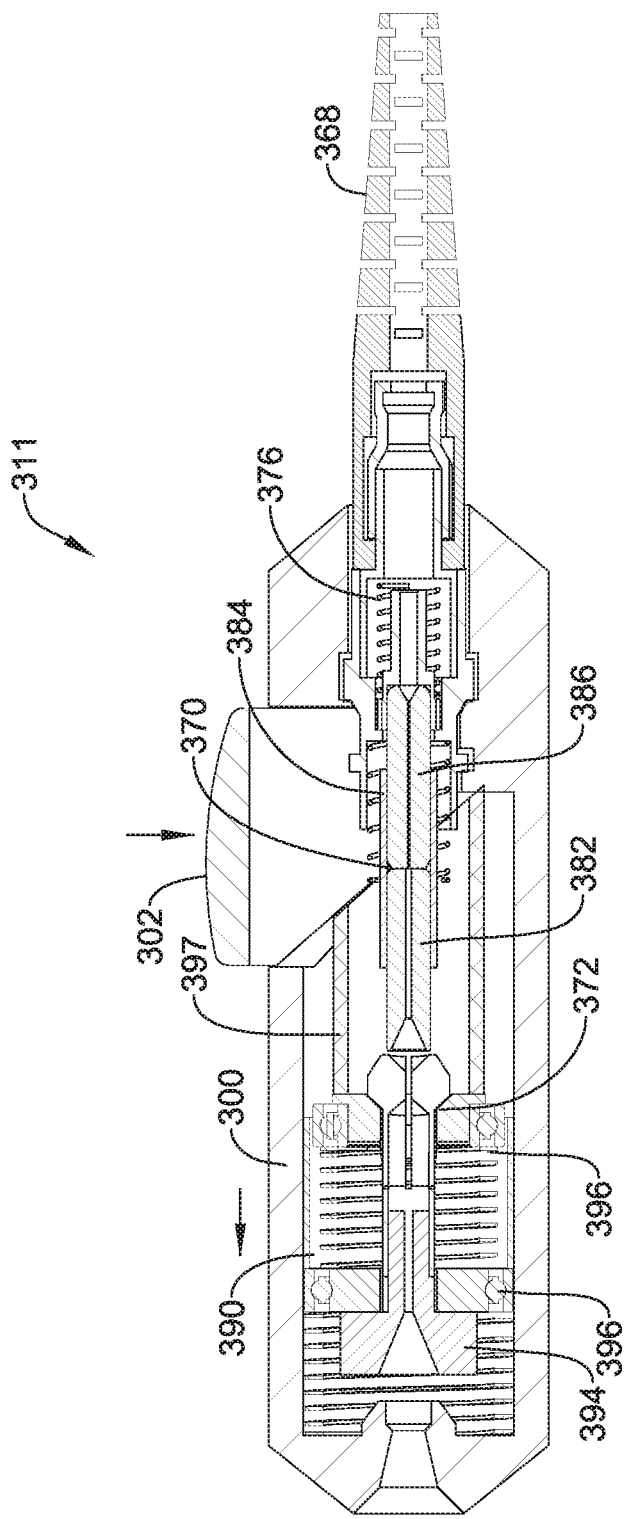
FIGS. 15-17 are partial cross-sectional side views of an example medical device system.

FIG. 15 is a partial cross-sectional view of an example medical device 311 before a guidewire has been inserted therein. In this figure, the actuator 302, in this embodiment, a button 302, has not been actuated, the collet spring 390 forces the inner housing 374 in a proximal direction and the collet 372 is in a closed state and the collet 372, guidewire 10 and collet retainer 374 are free to rotate.

Figure 16:
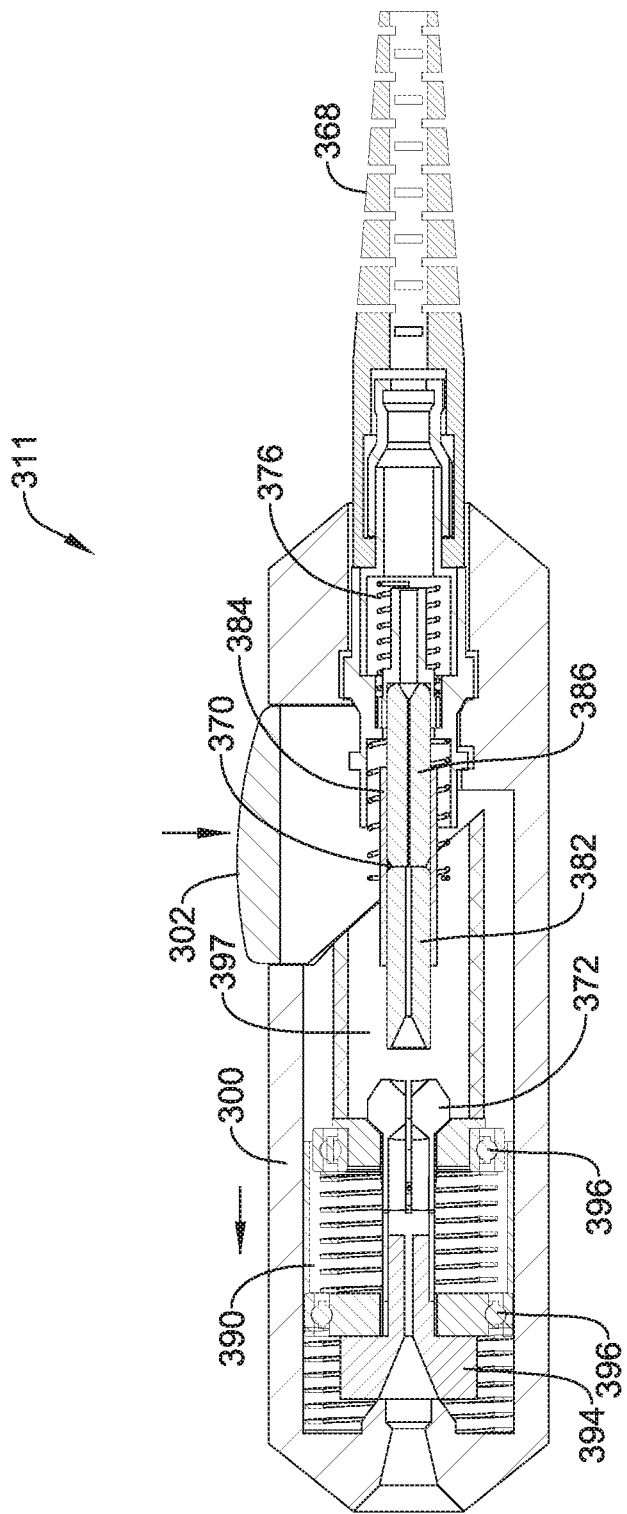
Figure 17:
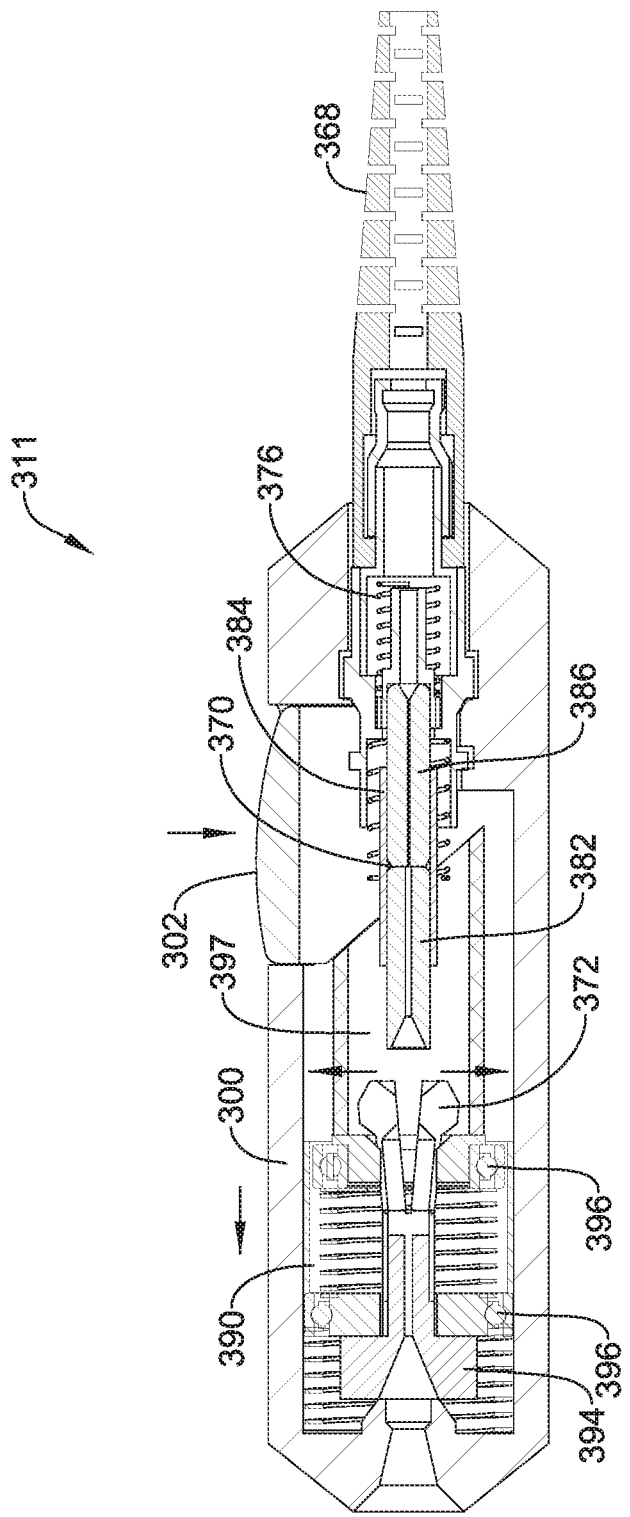

FIG. 16 is a partial cross-sectional view illustrating the partial depression of the actuator button 302 which pushes the inner housing 374 in a distal direction and the axial spring 392 collapses first. As the actuator button 302 is fully depressed as shown in FIG. 17, the collet spring 390 collapses allowing the collet 372 to open for insertion or removal of guidewire 10.

Figure 18:
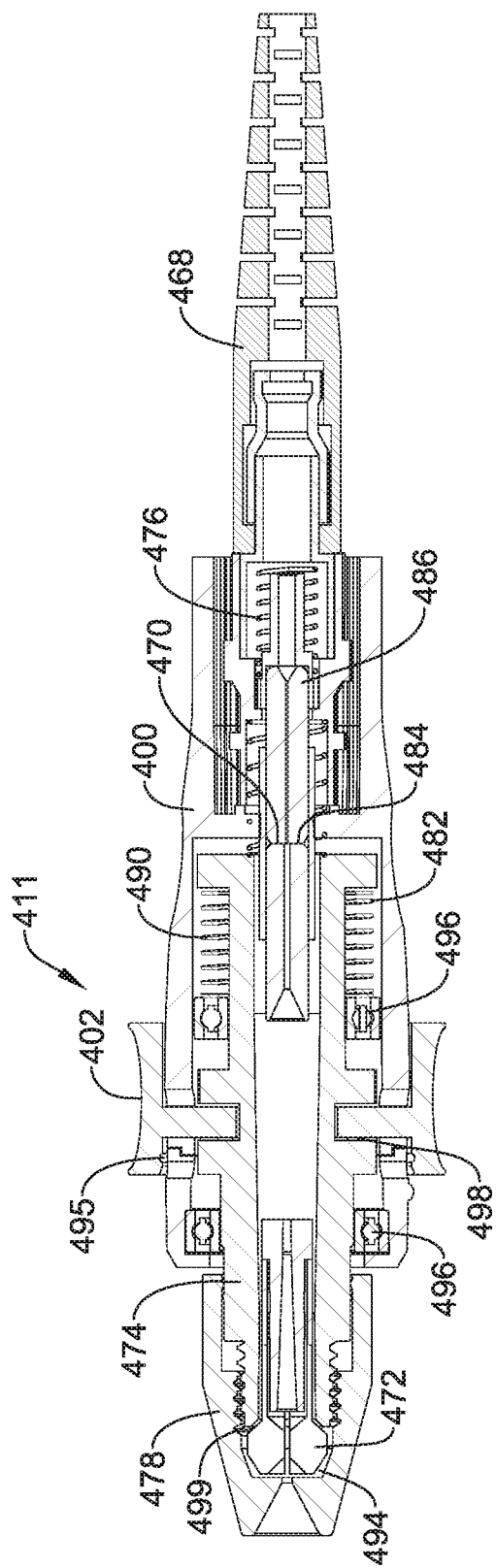
FIGS. 18 and 19 are partial cross-sectional side views of an example medical device system.

FIG. 18 is a partial cross-sectional view illustrating of an example medical device system 411 having a distal connector 466 and an optical connector cable 460. Housing 400 of distal connector further includes an inner housing 474 having a spline gear 498.

Figure 19:
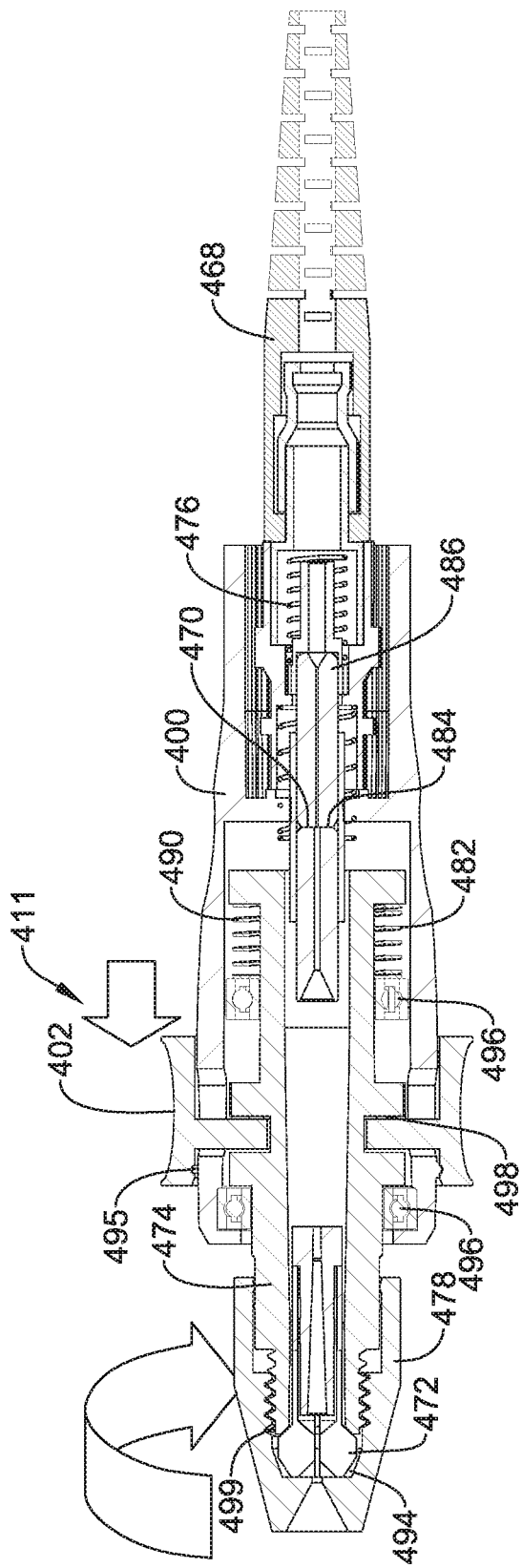

Spline gear 498 prevents inner housing 474 of distal connector 466 from rotating when the actuator 402, in this embodiment, a sliding mechanism, is pushed in a distal direction over a stop or detent 405 as shown in FIG. 19. Actuator 402 in its forward position, moves the inner housing 474 with spline gears 498 in a distal direction allowing rotation of the collet cap 478 for removal of the guidewire. The spline gear 498 of the inner housing 474 is in a locked position with matching grooves of inner housing 474 which prevents rotation of the inner housing 474.

Figure 20:
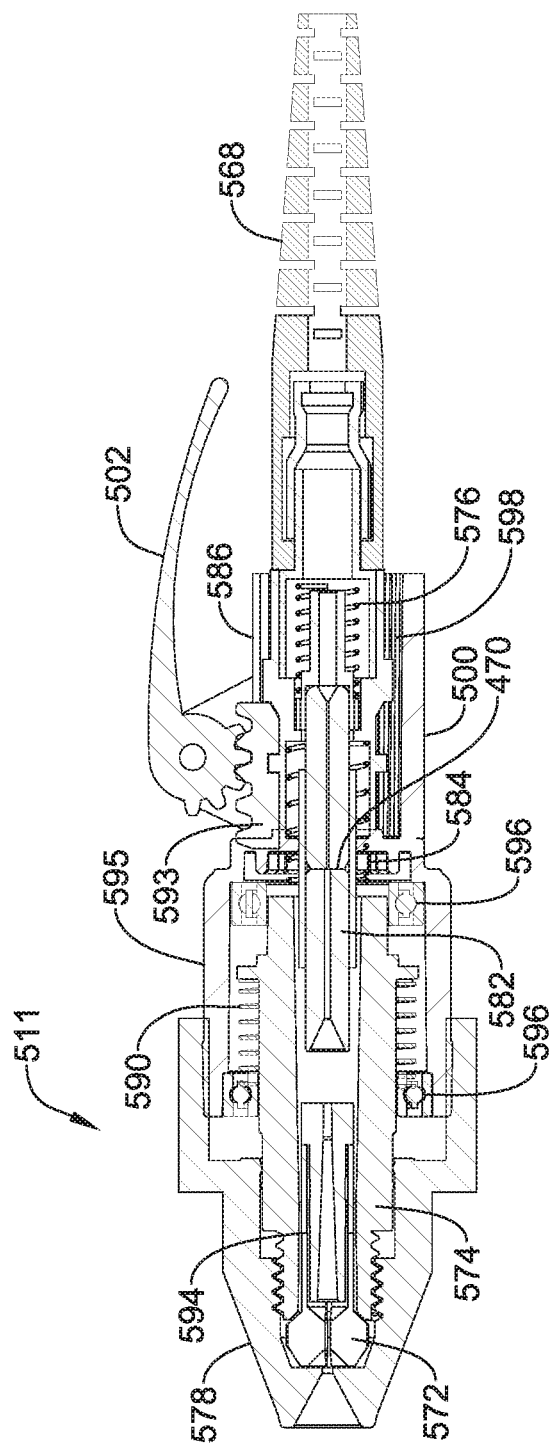
FIGS. 20 and 21 are partial cross-sectional side views of an example medical device system.

FIG. 20 is a partial cross-sectional view illustrating of an example medical device system 511 having a guidewire locking mechanism, a distal connector 566, and an optical connector cable 560. Housing 500 of distal connector further includes an inner housing 574 including a collet 572 and a collet retainer 594. In the resting state, an inner housing 597 coupled to an actuator prevents spline gear 598 from contacting inner housing 574 of distal connector 566 allowing for rotation of a guidewire relative to distal connector 566.

Figure 21:
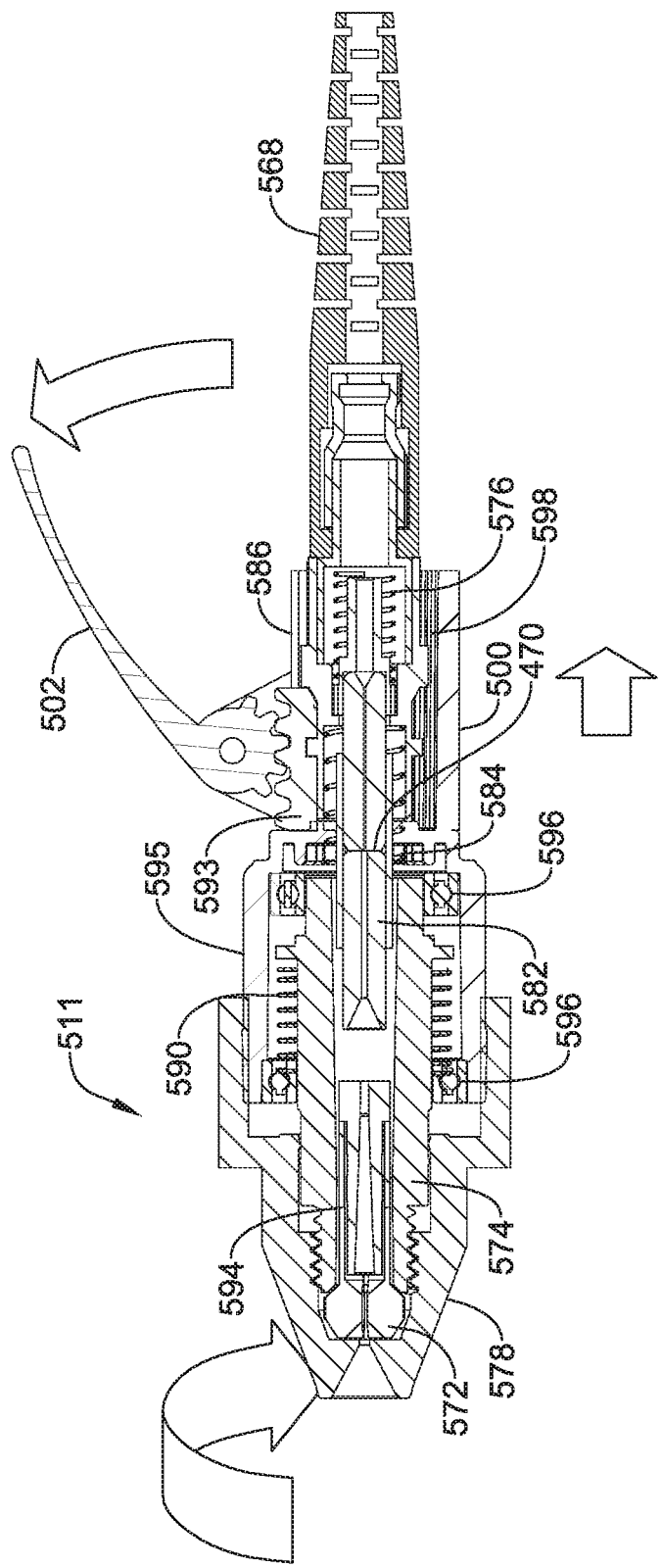

When actuator 502, in this case a lever, is pushed forward as shown in FIG. 21, the distal connector 566 is separated from the housing 597 and the housing 574 with matching groves contacts the spline gears 598 and the collet cap 578 can be rotated to open the collet 572 and release guidewire 10.

Figure 22:
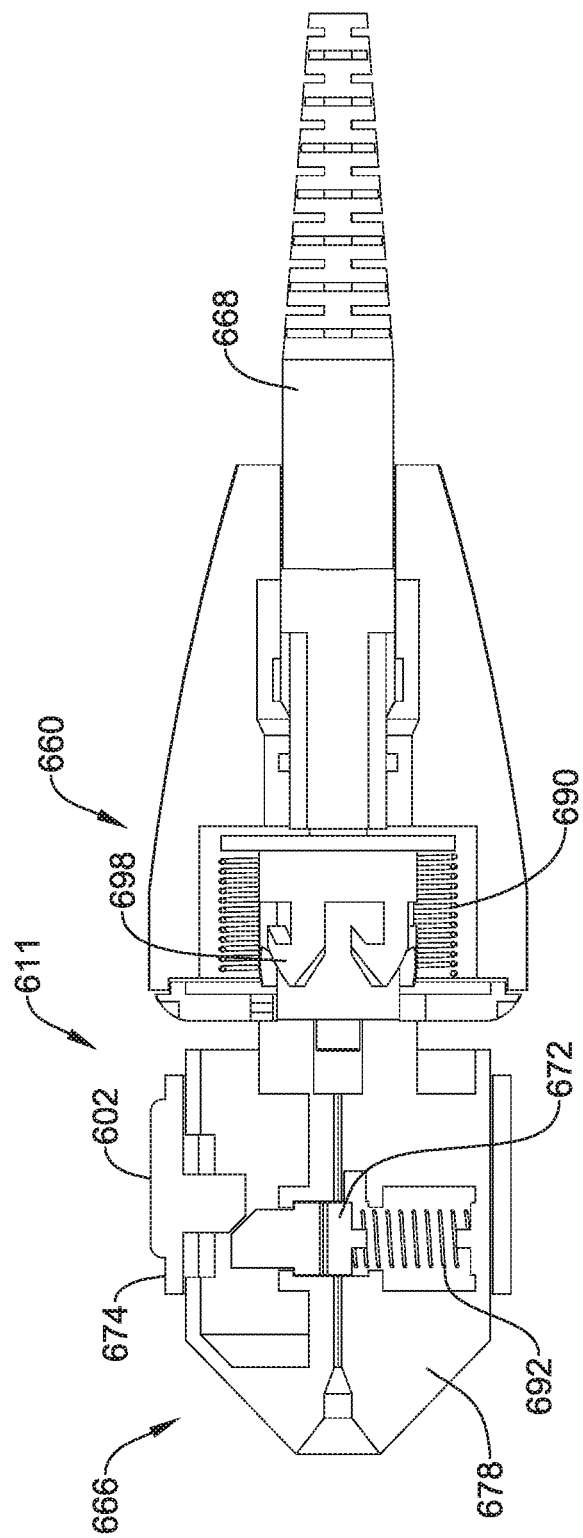
FIGS. 22 and 23 are partial cross-sectional side views of an example medical device system.
Figure 23:
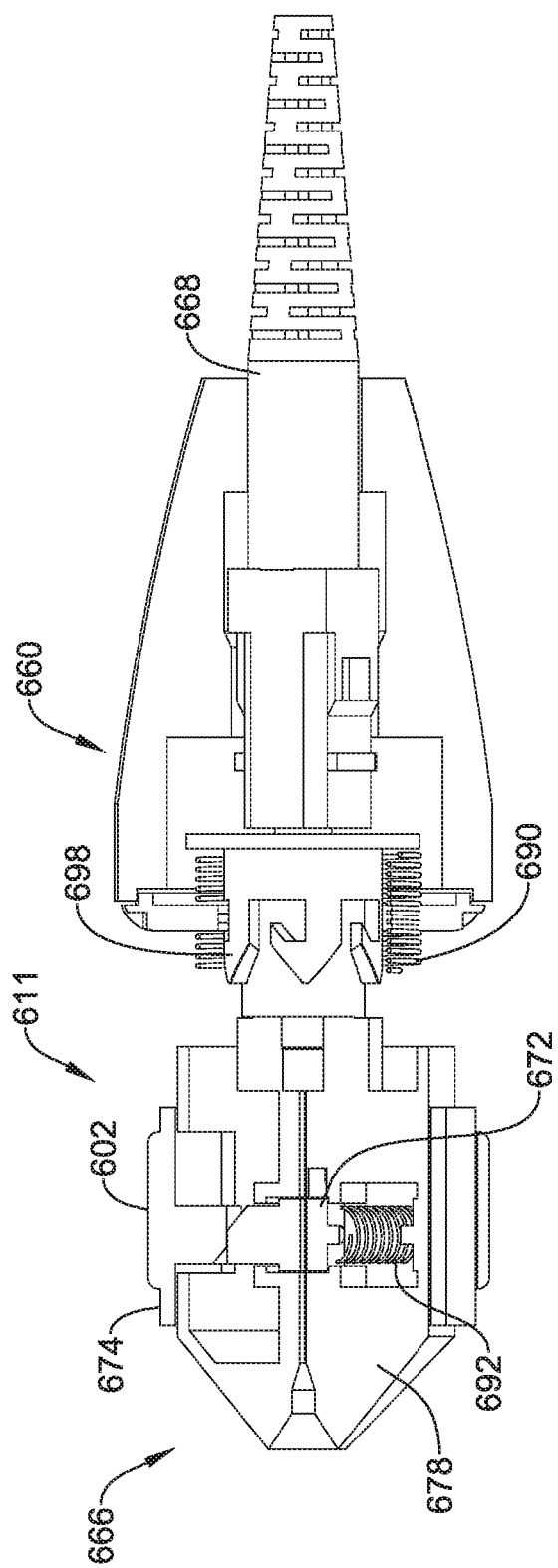

FIG. 22 is a partial cross-sectional view illustrating of an example medical device system 611 having a guidewire locking mechanism, a distal connector 666, and an optical connector cable 661. Distal connector 666 includes an actuator 602 for actuation of inner housing 674, a housing 600 having a locking pin 698 and a guidewire locking mechanism, in this embodiment, in the form of an offset pinch clamp 672. The offset pinch clamp 672 is in a closed state when the actuator 602, the inner housing 674, and the locking pin 698 are in the distal position. When actuator 602 is moved proximally as shown in FIG. 23, the inner housing is actuated, the locking pin engages and is seated within the grooves of gear 690 allowing rotation of the cap 678 and opening of the offset pinch clamp 272 for removal or insertion of a guidewire 10.

Figure 24:
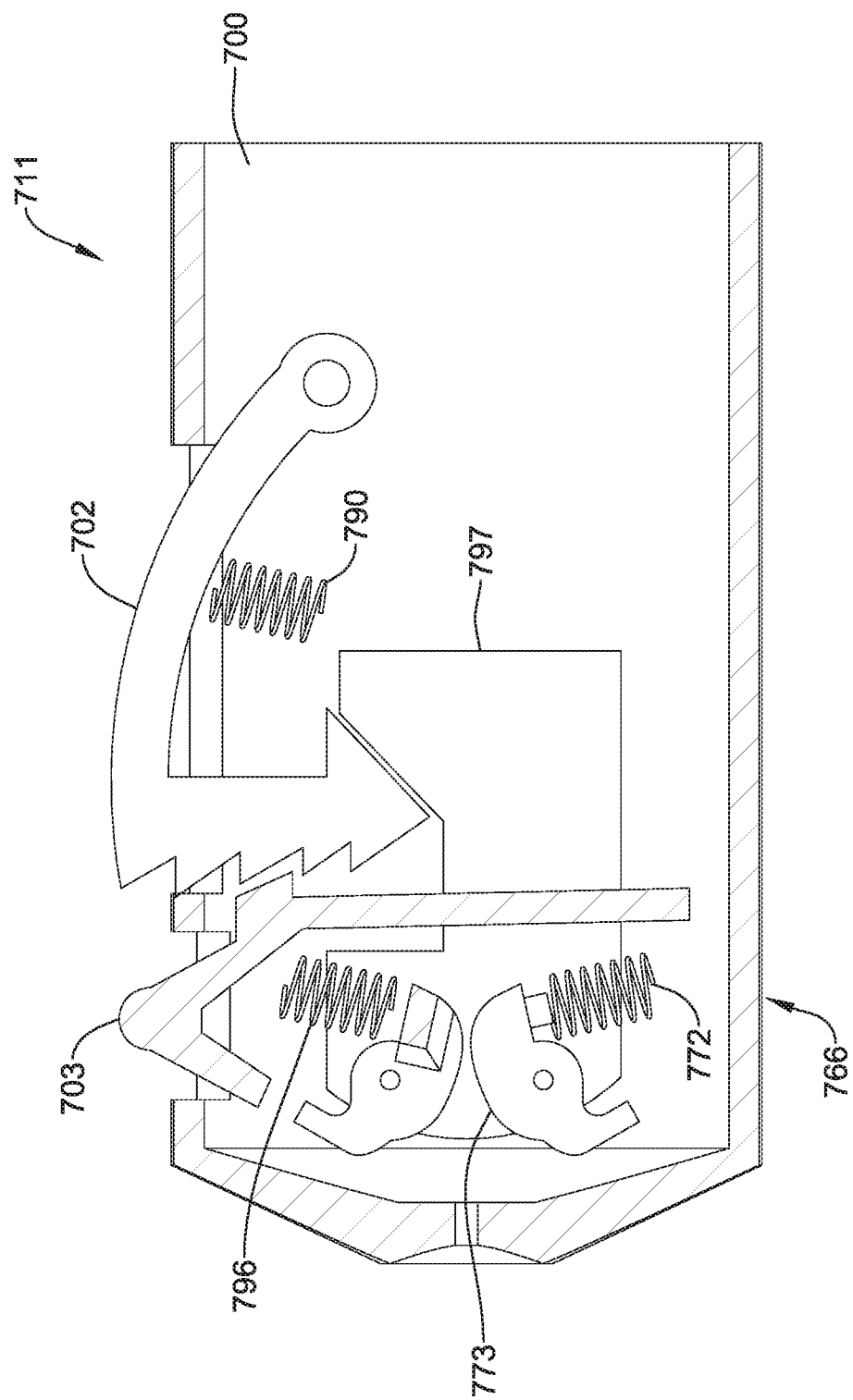
FIGS. 24-26 are partial cross-sectional side views of an example medical device system.
Figure 25:
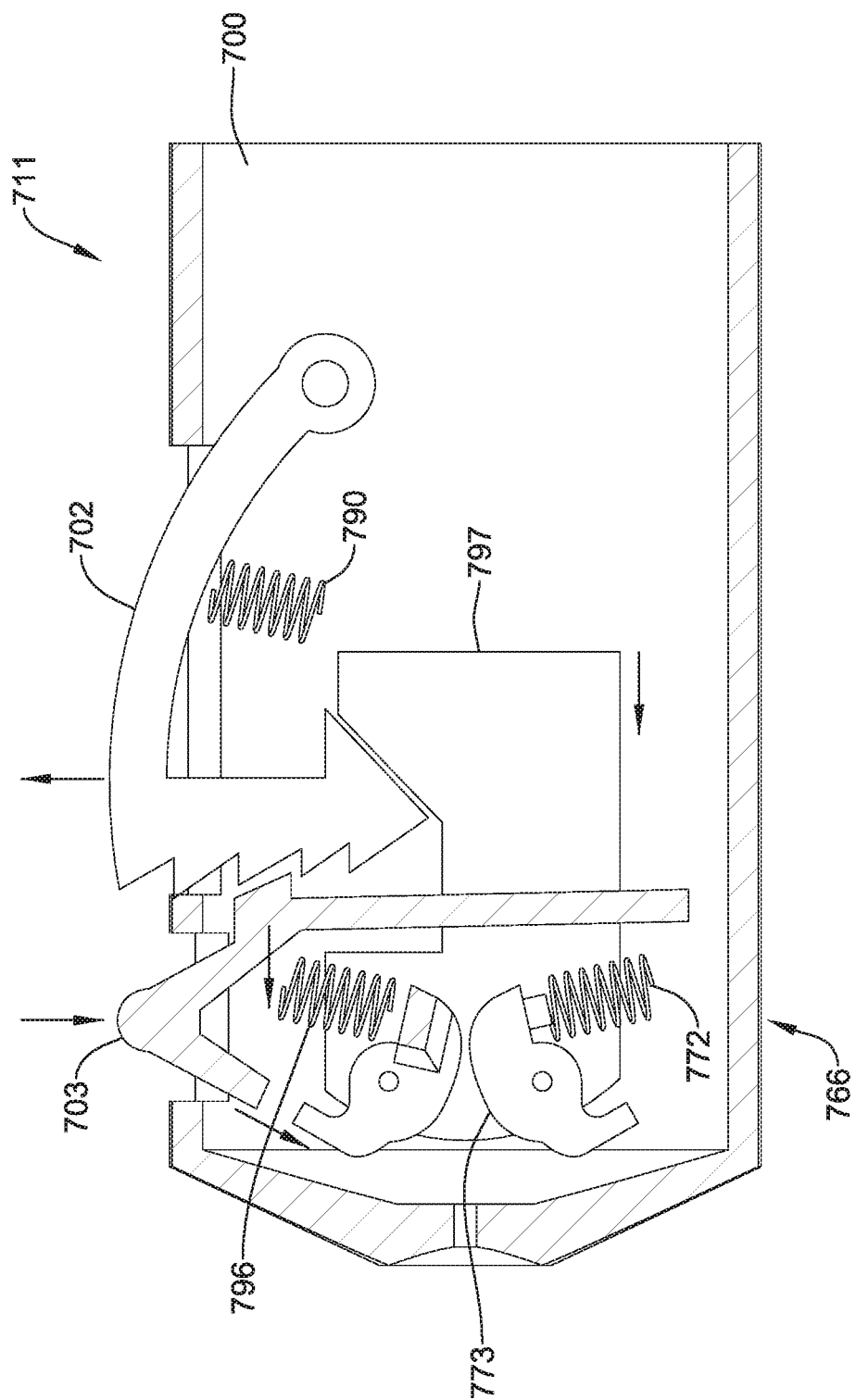
Figure 26:
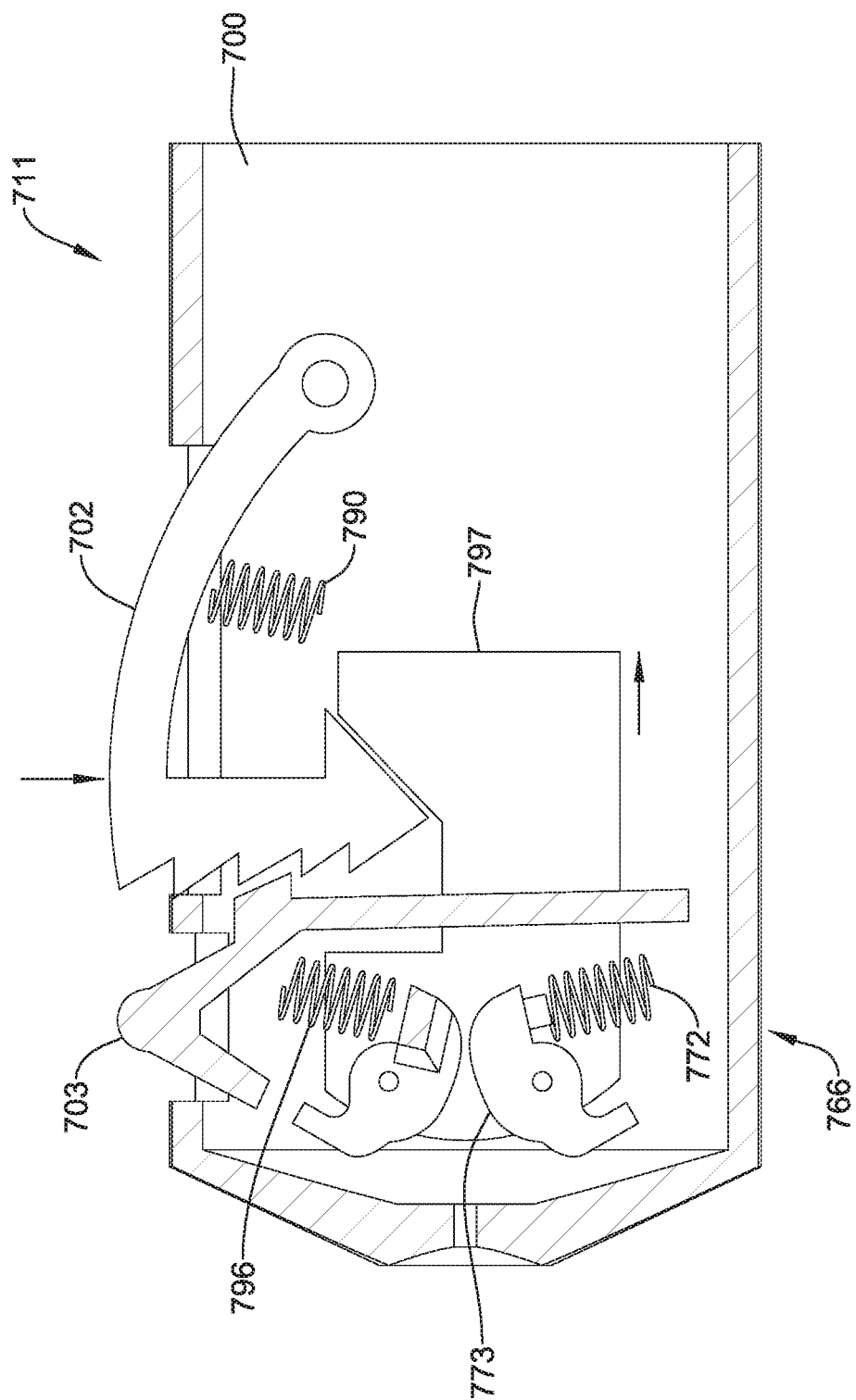

FIG. 24 is a partial cross-sectional view illustrating of an example medical device system 711 having a guidewire locking mechanism and a distal connector 766. Distal connector 766 includes a housing 700 with an inner housing 797 having a spring loaded cam assembly including springs 772 and cams 773. The cams 773 of the cam assembly allow rotation of the guidewire 10 while sufficiently locking the guidewire 10 to the distal connector 766. The actuator includes a ratchet 702 and a release button 703. When the ratchet 702 is compressed, the cams 773 are compressed and the guidewire 10 is pressed against the wire ferrule (not shown). When the release button 703 is compressed as shown in FIG. 25, the ratchet 702 releases and the cam assembly 772 returns to a resting state which frees the guidewire 10. This allows removal or insertion of the guidewire as shown in FIG. 26.

The materials that can be used for the various components of guidewire 10 (and/or other guidewires disclosed herein) and the various tubular members disclosed herein may include those commonly associated with medical devices. For simplicity purposes, the following discussion makes reference to shaft 12 and other components of guidewire 10. However, this is not intended to limit the devices and methods described herein, as the discussion may be applied to other similar tubular members and/or components of tubular members or devices disclosed herein.

The various components of the devices/systems disclosed herein may include a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

U.S. Patent Application Publication No. U.S. 2014/0350414 is herein incorporated by reference. U.S. Patent Application Publication No. U.S. 2014/0058275 is herein incorporated by reference. U.S. patent application Ser. No. 14/196,740 filed Mar. 4, 2014 is herein incorporated by reference.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. An optical connector cable assembly, comprising:
   an optical connector cable comprising a first optical fiber extending therefrom;
   wherein the optical connector cable includes a distal connector configured to connect to a guidewire, the distal connector comprising an inner housing and a guidewire locking mechanism;
   an actuator disposed on the distal connector, wherein the actuator includes a slidable member that is slidable along the distal connector and wherein actuation of the actuator moves the inner housing from a first position to a second position;
   wherein when the inner housing is in the first position the guidewire locking mechanism is configured to secure the guidewire and the guidewire is rotatable with respect to the optical connector cable; and
   wherein when the inner housing is in the second position the guidewire locking mechanism is in an open state for receiving or removing the guidewire.

2. The optical connector cable assembly of claim 1, wherein the guidewire locking mechanism includes a collet closer.

3. The optical connector cable assembly of claim 2, wherein the guidewire locking mechanism further comprises a collet spring and a collet.

4. The optical connector cable assembly of claim 1, wherein the guidewire locking mechanism includes a spring loaded cam assembly.

5. The optical connector cable assembly of claim 1, further comprising an axial spring adjacent the inner housing, when the inner housing is in the second position, the axial spring collapses allowing the guidewire locking mechanism to open.

6. The optical connector cable assembly of claim 1, wherein the inner housing further comprises a spline gear, when the inner housing is in the second position, the spline gear prevents the inner housing from rotating relative to the optical connector cable.

7. The optical connector cable of claim 6, further comprising a collet and a collet cap, when the inner housing is in the second position, the collet cap can be rotated relative to the optical connector cable.

8. The optical connector cable assembly of claim 1, wherein the guidewire locking mechanism includes an offset pinch clamp.

9. A medical device system for measuring blood pressure, the system comprising:
   an optical connector cable including a first optical fiber and a distal connector comprising an inner housing and a guidewire locking mechanism, the distal connector capable of being coupled to a pressure sensing guidewire;
   the pressure sensing guidewire including a pressure sensor and a second optical fiber extending proximally from the pressure sensor, the second optical fiber being capable of optically communicating with the first optical fiber, wherein the optical connector cable is designed to be coupled to the pressure sensing guidewire; and
   an actuator comprising a sliding mechanism that is slidable along the distal connector, wherein actuation of the actuator moves the inner housing from a first position to a second position, wherein when the inner housing is in the first position the guidewire locking mechanism is in a closed state for retaining the pressure sensing guidewire and the pressure sensing guidewire is rotatable with respect to the optical connector cable, and wherein when the inner housing is in the second position the inner housing is moved in a distal direction from the optical connector cable and the guidewire locking mechanism is in an open state for receiving or removing the pressure sensing guidewire.

10. The system of claim 9, wherein the guidewire locking mechanism includes a collet closer.

11. The system of claim 10, wherein the guidewire locking mechanism further comprises a collet spring and a collet, when the inner housing is in the second position, the collet spring is compressed allowing the collet to open, and when the inner housing is in the first position, the collet spring closes the collet closer.

12. The system of claim 9, wherein the guidewire locking mechanism includes a spring loaded cam assembly.

13. The system of claim 9, further comprising an axial spring adjacent the inner housing, when the inner housing is in the second position, the axial spring collapses allowing the guidewire locking mechanism to open.

14. The system of claim 9, wherein the inner housing further comprises a spline gear, when the inner housing is in the second position, the spline gear prevents the inner housing from rotating relative to the optical connector cable.

15. The system of claim 14, further comprising a collet and a collet cap, when the inner housing is in the second position, the collet cap may be rotated relative to the optical connector cable.

16. The system of claim 9, wherein the guidewire locking mechanism includes an offset pinch clamp.

17. An optical connector cable, comprising:
a distal connector comprising an inner housing and a guidewire locking mechanism, the distal connector capable of being coupled to a guidewire; and
an actuator comprising an axially translatable member slidable along the distal connector, wherein actuation of the actuator moves the inner housing of the distal connector from a first position to a second position, wherein when the inner housing is in the first position the guidewire locking mechanism is in a closed state for retaining the guidewire and the guidewire is rotatable with respect to the optical connector cable, and wherein when the inner housing is in the second position the inner housing is moved in a distal direction from the optical connector cable and the guidewire locking mechanism is in an open state for receiving or removing the guidewire.

18. The optical connector cable of claim 17, wherein the distal connector further comprises an axial spring adjacent the inner housing, when the inner housing is in the second position, the axial spring collapses allowing the guidewire locking mechanism to open.

\* \* \* \* \*